United States Patent [19]

Resnick et al.

[11] 4,207,554
[45] Jun. 10, 1980

[54] METHOD AND APPARATUS FOR AUTOMATED CLASSIFICATION AND ANALYSIS OF CELLS

[75] Inventors: Jerome B. Resnick, Trenton, N.J.; John W. Combs, Annville, Pa.

[73] Assignee: Med-El Inc., Princeton, N.J.

[21] Appl. No.: 936,487

[22] Filed: Aug. 24, 1978

Related U.S. Application Data

[60] Division of Ser. No. 596,964, Jul. 17, 1975, Pat. No. 4,125,828, which is a continuation-in-part of Ser. No. 277,992, Aug. 4, 1972, abandoned.

[51] Int. Cl.² .................. G02B 21/34; G06K 9/00
[52] U.S. Cl. .......................... 340/146.3 CA; 350/92
[58] Field of Search .................. 340/146.3 CA; 350/92

[56] References Cited

U.S. PATENT DOCUMENTS

| | | | |
|---|---|---|---|
| 2,801,568 | 8/1957 | Dakin | 350/92 |
| 3,498,860 | 3/1970 | Pickett | 350/92 |
| 3,577,267 | 5/1971 | Preston, Jr. et al. | 350/92 |
| 3,633,991 | 1/1972 | Miller | 350/92 |
| 4,087,154 | 5/1978 | Menzel | 350/92 |

*Primary Examiner*—Leo H. Boudreau

[57] ABSTRACT

Cells are automatically classified and analyzed by staining a measured amount of a specimen with a material which is adapted to fluoresce when illuminated; preparing a slide containing the stained specimen; illuminating the slide with light of successively changing wavelengths to measure the presence of the fluorescent response at each of the predetermined wavelengths to determine the constituents of the specimen.

The detected constituents are automatically focused and scanned by a microscope having a capability of locating the constituent of interest, determining its size, shape and texture to thereby provide information as to the type, count and the like to enable a detailed analysis of the specimen.

10 Claims, 23 Drawing Figures

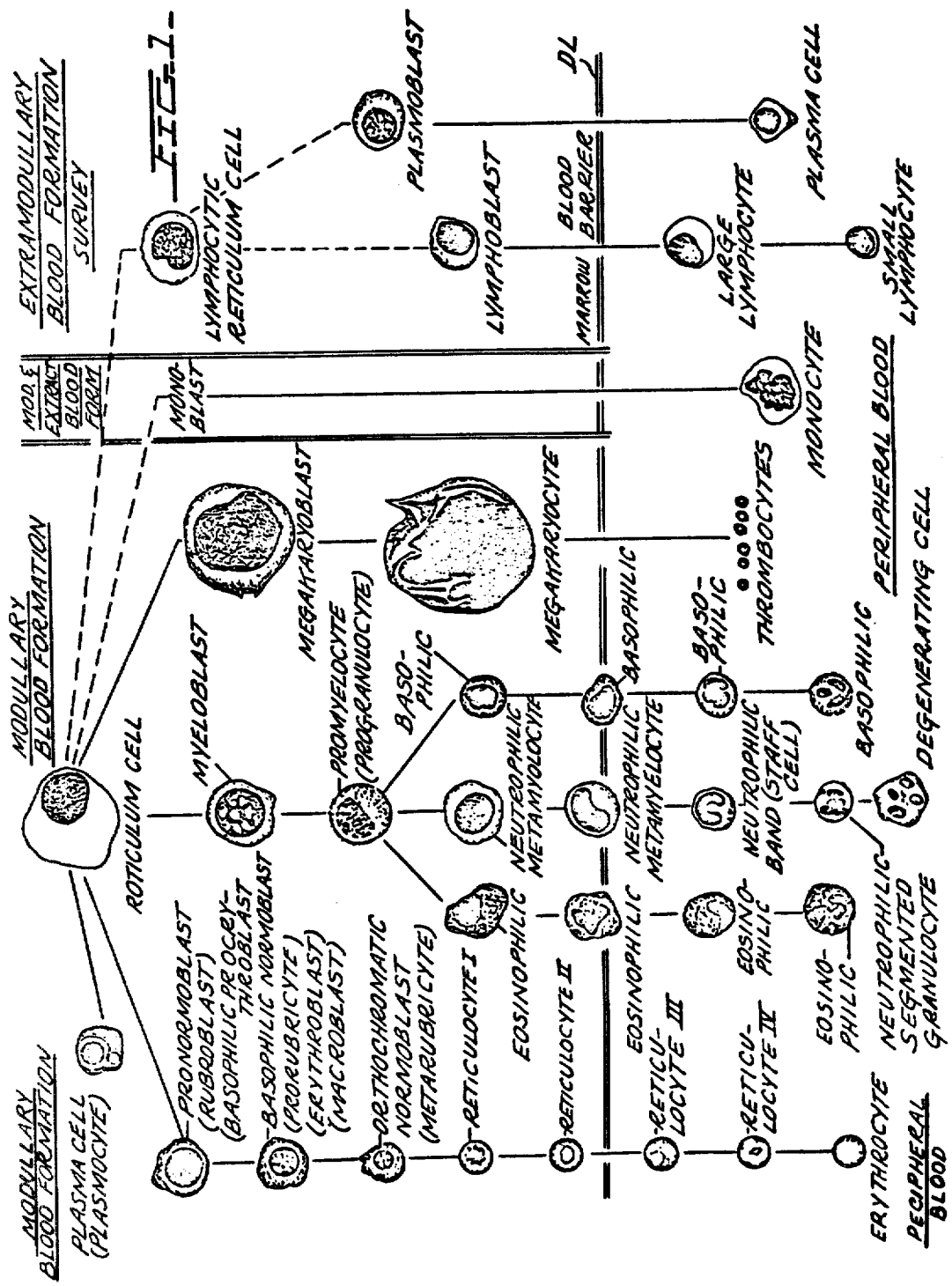

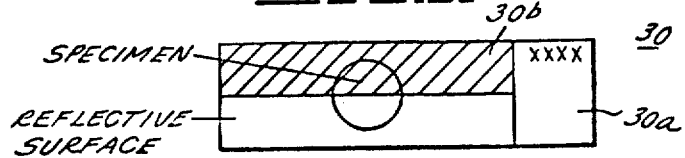
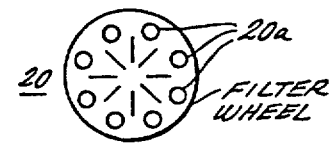
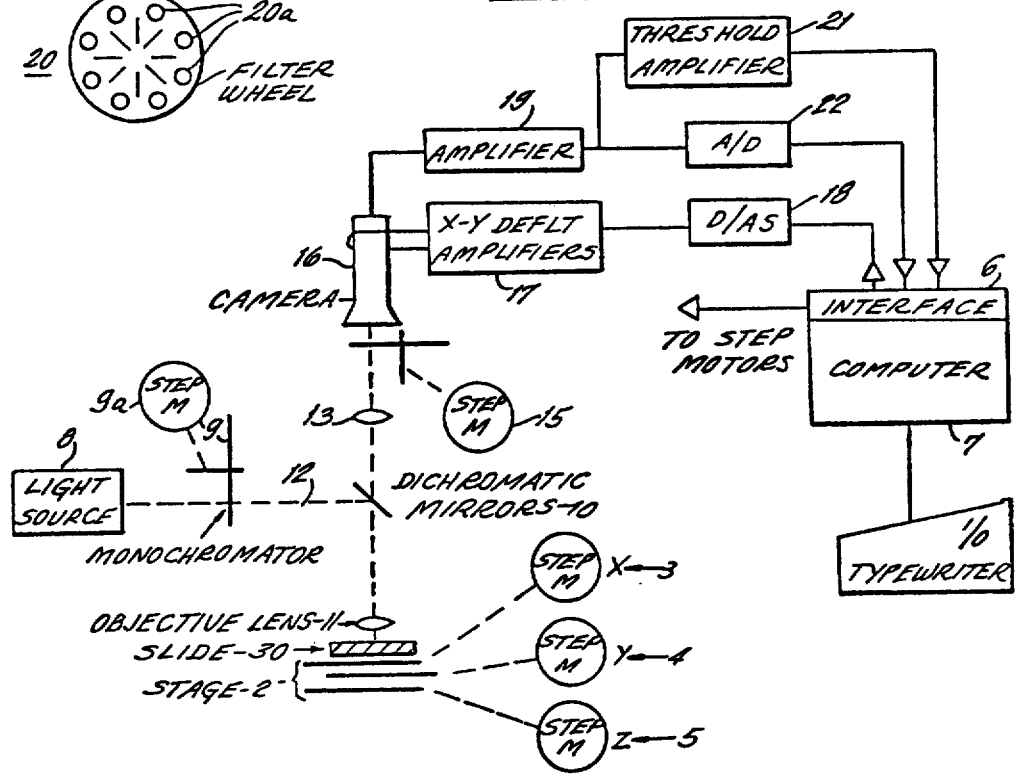
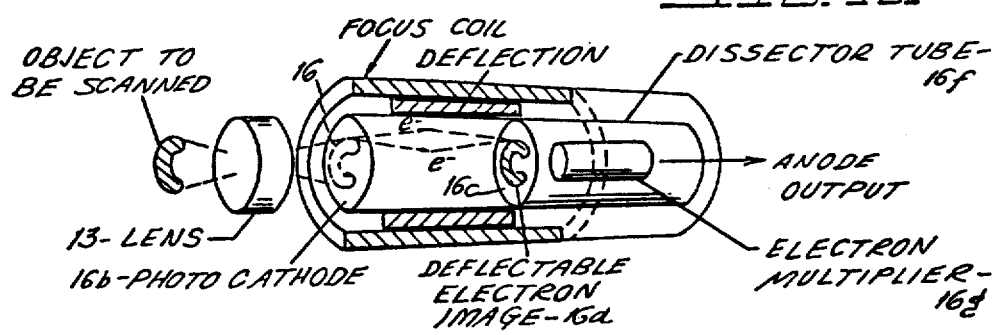

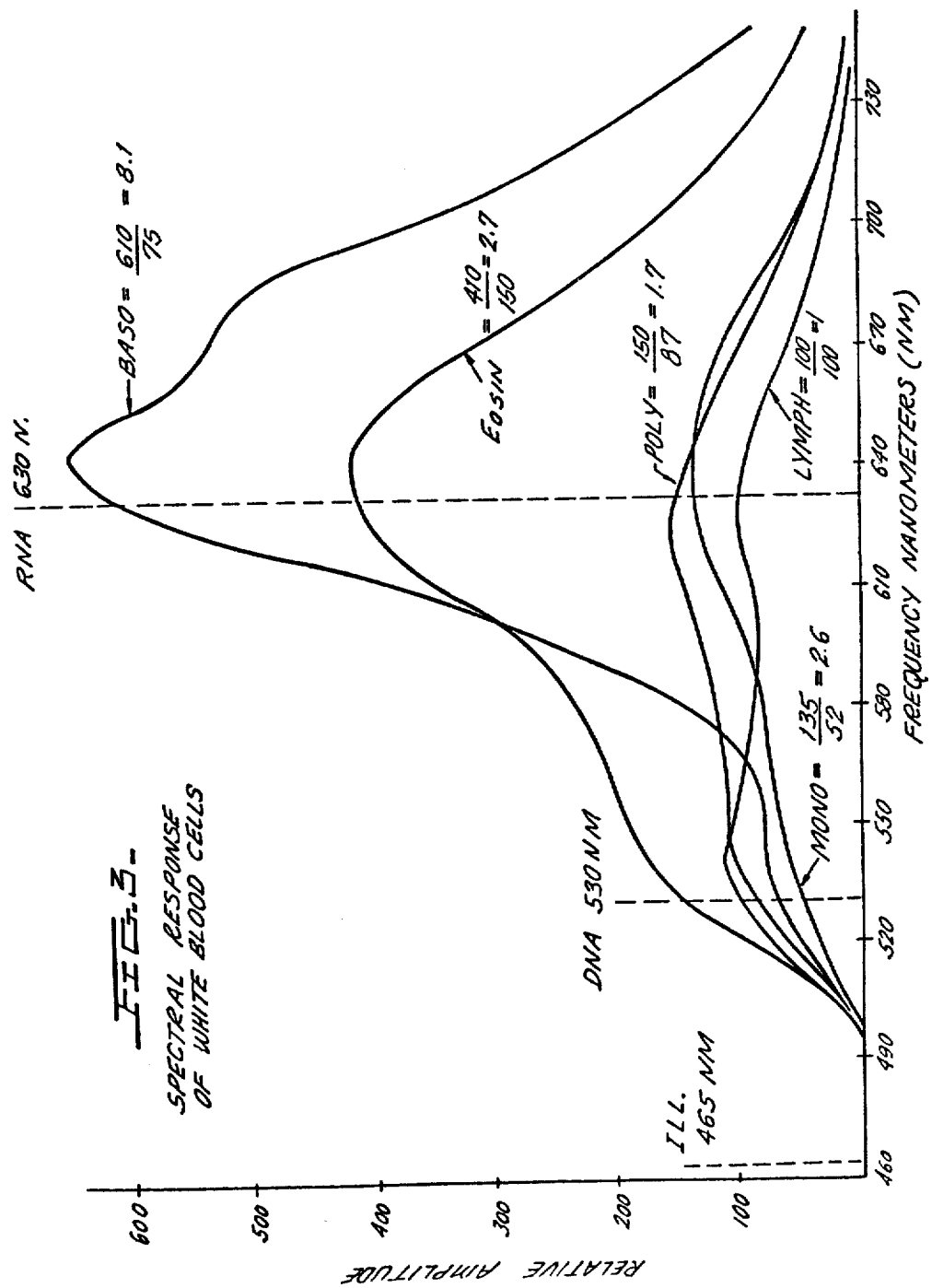

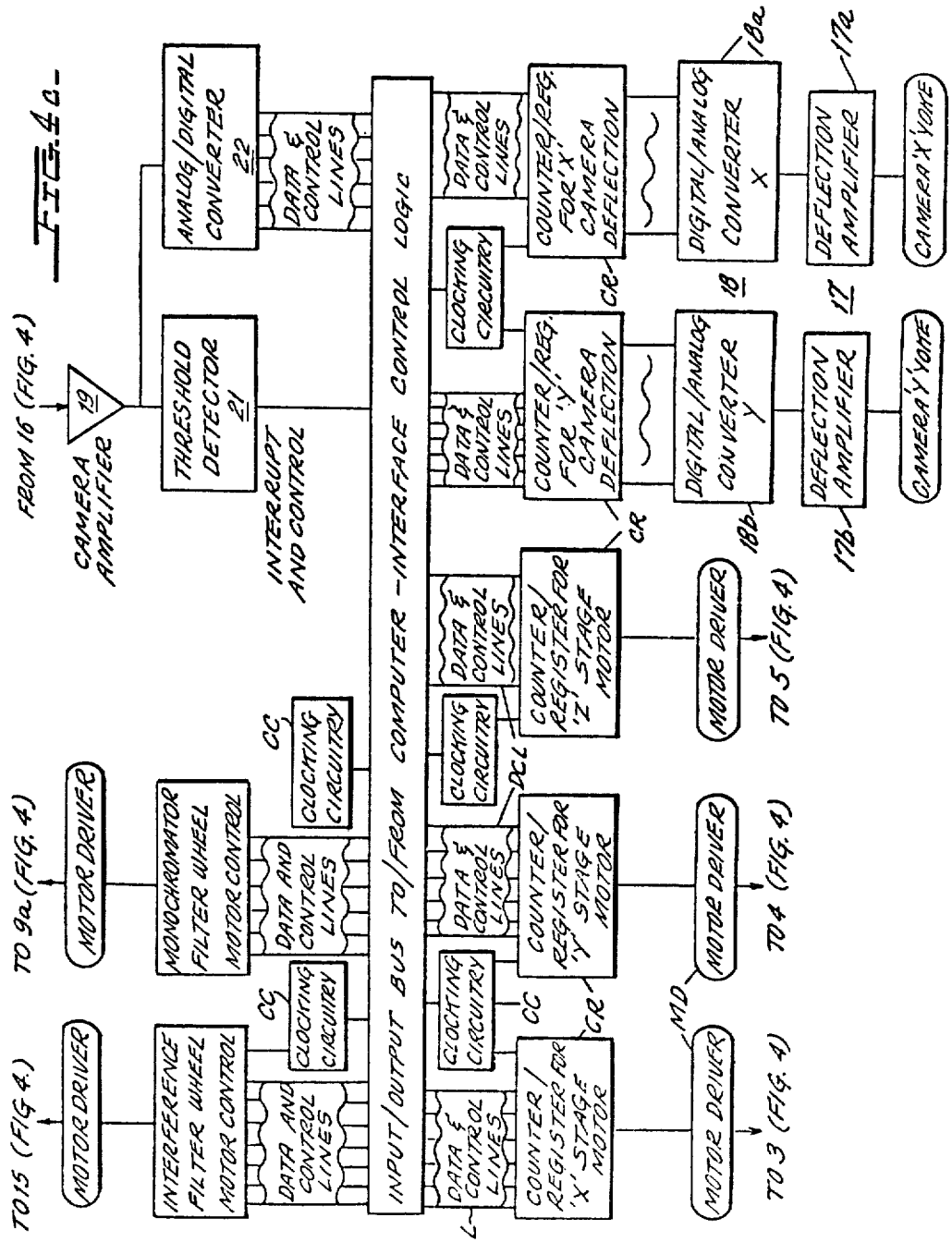

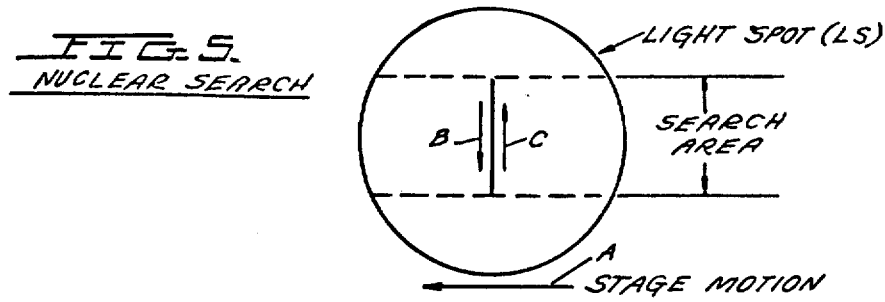
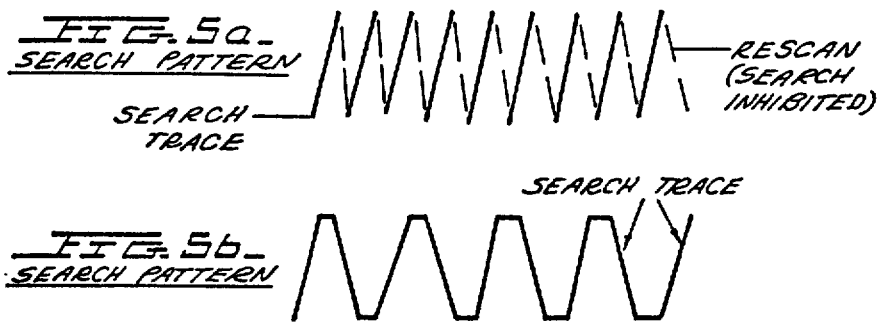
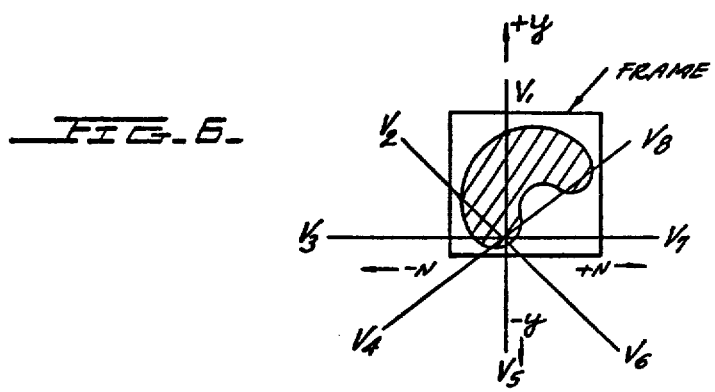
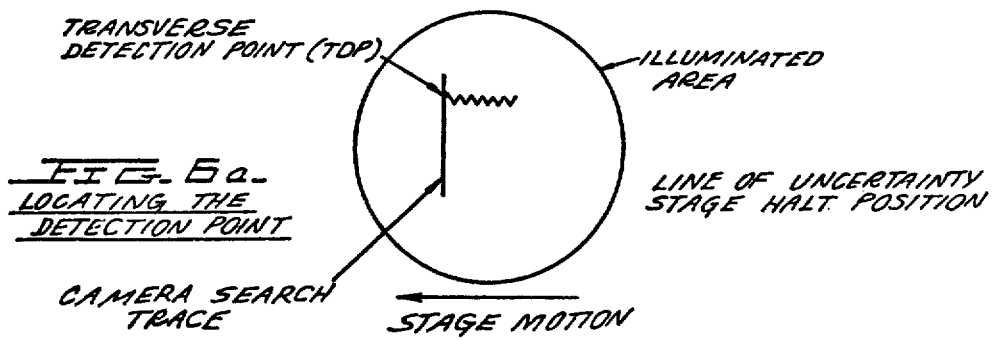

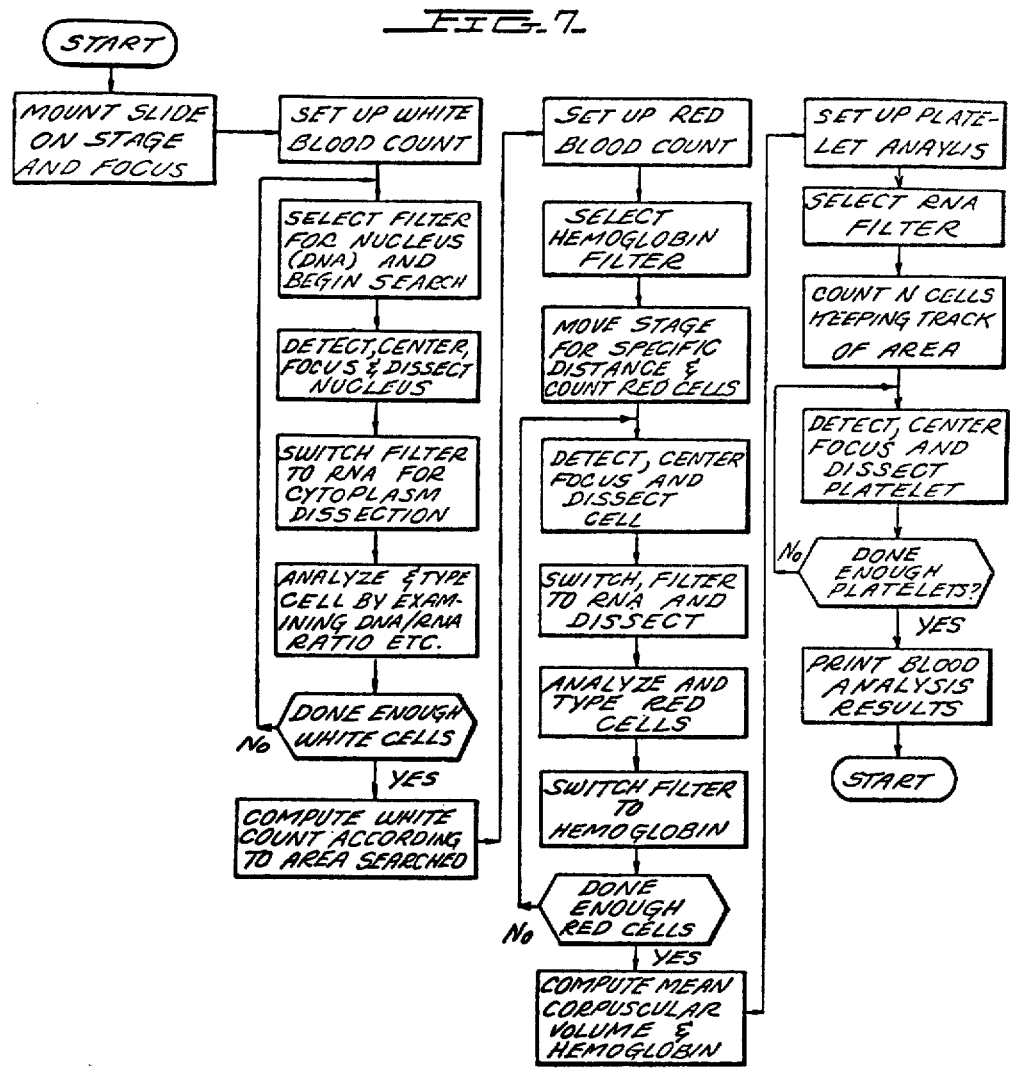
FIG. 7.
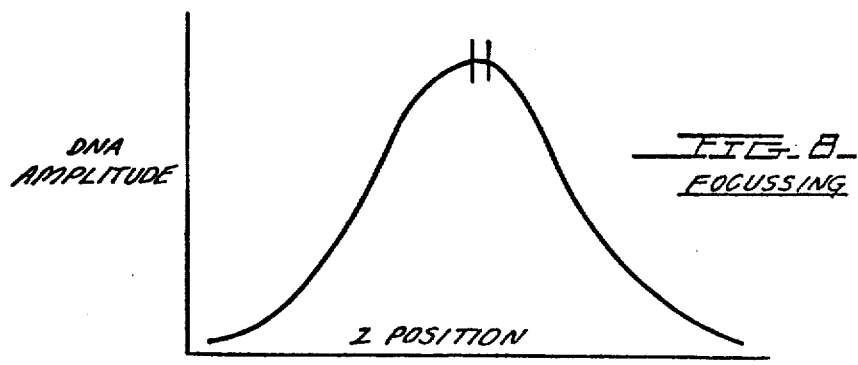
FIG. 8. FOCUSSING

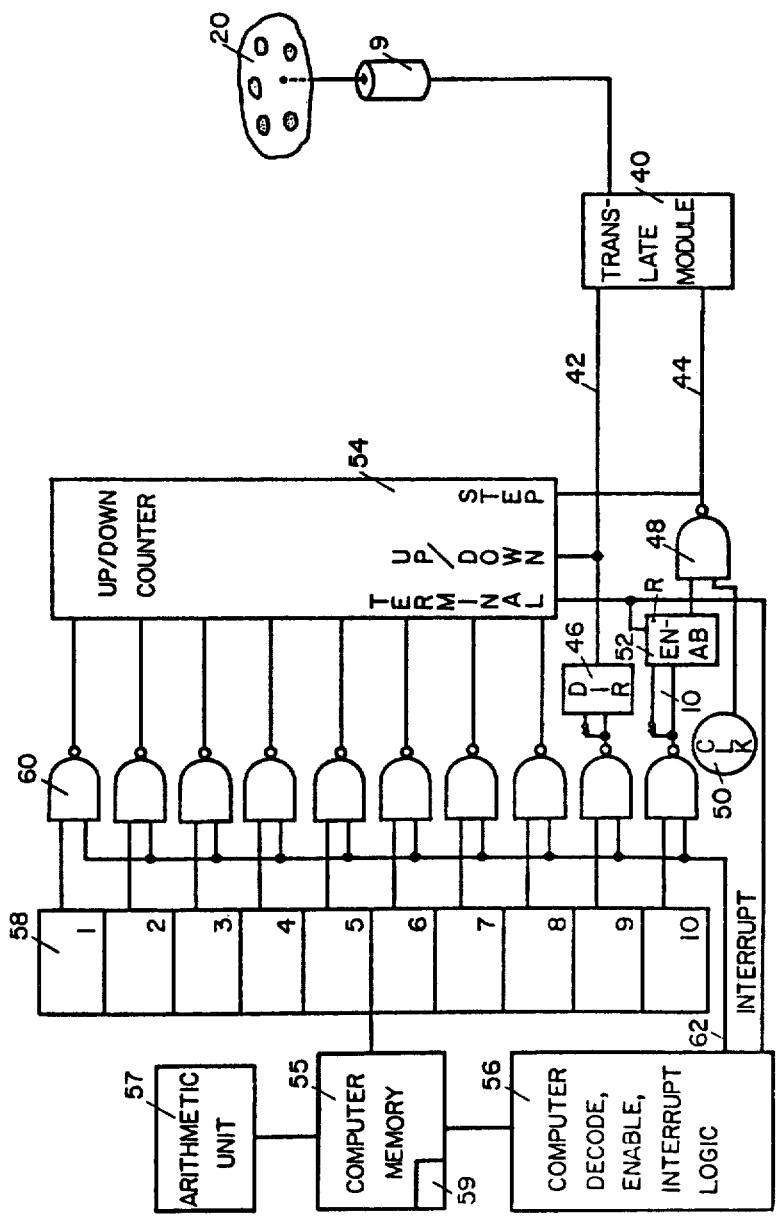

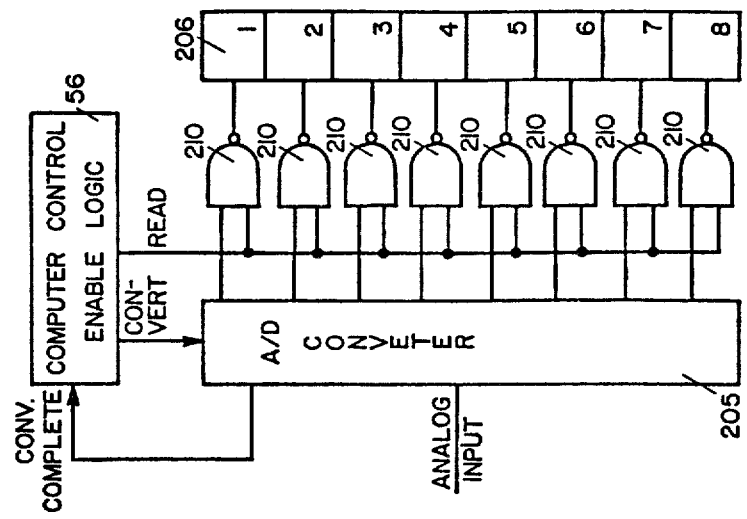
FIG. 16 A/D CONVERSION
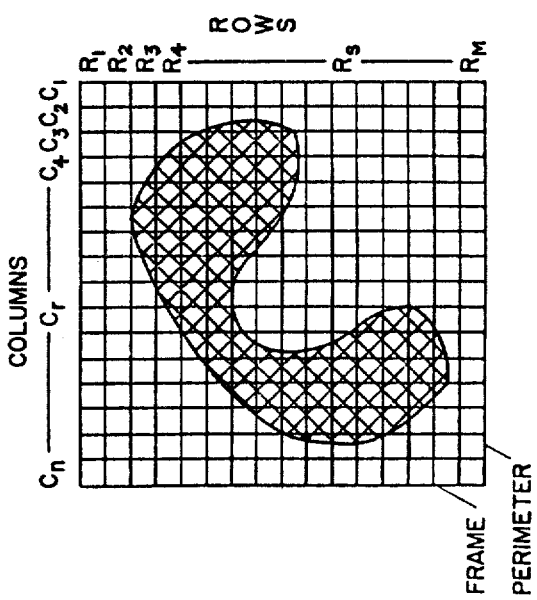
FIG. 15 WBC DISSECTION

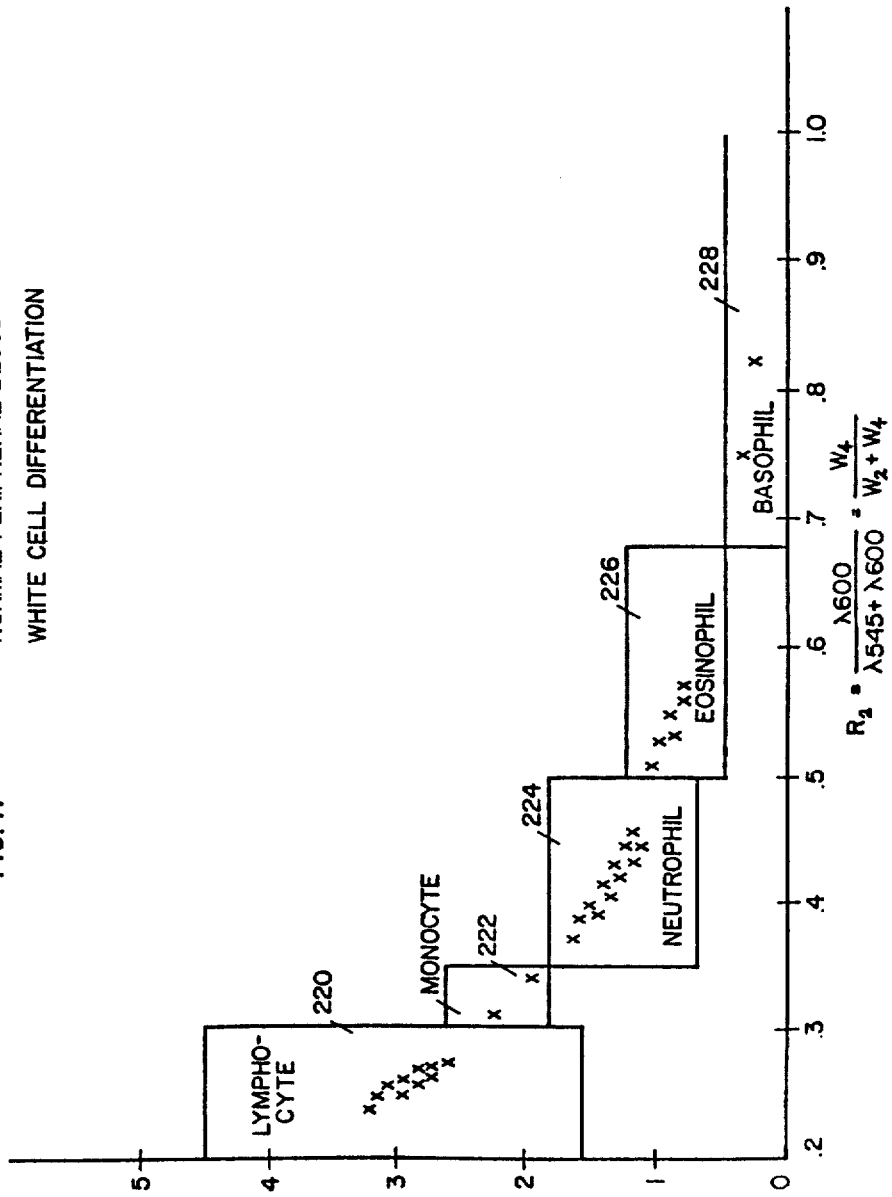
FIG. 17 NORMAL PERIPHERAL BLOOD WHITE CELL DIFFERENTIATION

METHOD AND APPARATUS FOR AUTOMATED CLASSIFICATION AND ANALYSIS OF CELLS

CROSS REFERENCE TO RELATED APPLICATIONS

This is a division of application Ser. No. 596,964, filed July 17, 1975, now U.S. Pat. No. 4,125,828, which is a continuation in part of application Ser. No. 277,992 filed Aug. 4, 1972, now abandoned.

BACKGROUND OF THE INVENTION

In recent years much has been accomplished in the automation of various bioclinical laboratory procedures. One area in which little progress has been made is in the classification and analysis of cells. The need for the automation of blood cell analysis is manifest. Present day techniques are fragmented, manual (and hence tedious and susceptible to human error), expensive and often inaccurate. They are at best marginally satisfactory in their ability to cope with the large volume demands on the clinical laboratory for blood cell classification.

The analysis of the formed elements (cells and platelets) found in human blood comprises the most common set of laboratory tests required by doctors. These tests are of critical clinical importance both as a screening mechanism and as a means of following the course of a wide variety of diseases, including anemias, infections, heart attacks, damage to body tissues, allergies, etc. Blood tests are also used to monitor the effects of therapeutic agents.

In the case of disorders of the blood and blood forming organs (hematologic diseases), blood analysis is the primary diagnostic tool available to the physician. At present the hematologic diseases, especially leukemia, are poorly characterized and often pose difficult diagnostic problems, based, in part, on the inadequacy of current manual microscope blood testing methods. The human technologist, no matter how well trained, can only obtain certain kinds of qualitative information about blood cells by looking at them through a microscope. It is often precisely the variations in the subjective interpretation of this qualitative information (such as the details of the distribution of stained materials in the cell or cell nucleus) that forms the basis of controversy among hematologic experts regarding important diagnostic distinctions as leukemia versus some temporary condition, such as an infection.

A complete blood count (CBC) consists of a red cell (RBC) count, a white cell (WBC) and a differential white cell count. The RBC and WBC counts indicate the total number of red and white cells, respectively, per unit volume of blood. The differential white cell count indicates the relative number of the different types of white cells which make up the white cell count.

At present this most complex portion of blood analysis is performed manually using conventional microscopes to examine and count the cells of each specimen. A hematology technician performing a differential blood count identifies and counts cells and notes the presence of abnormal cells. When abnormal (usually immature) cells are present as indicated by the technician, the specimen is examined by a pathologist or hematologist who attempts to arrive at a diagnosis of the disease that caused the appearance of the abnormal cells. This detailed examination is time consuming and based mainly on subjective impressions.

The length of time required to train a technician to perform differential blood counts with reasonable proficiency is on the order of several weeks. The technician counts and identifies a large number of cells. These are identified by comparison with a set of loosely defined "standards"—requiring subjective judgments which inherently lead to differences in cell counts between technicians. Typically, 5 to 10 minutes are required for a differential count. A technician can perform approximately 30 differential counts per day. Continuous peering into a microscope and counting cells quite often leads to weariness and carelessness which results in incorrect counts. The differential count is probably the longest and most difficult routine task still being performed by technicians in the clinical laboratory.

The frequency of performance of this type of diagnostic test has increased more than 100% in the last ten years. It is estimated that more than 200,000 differential blood counts are performed daily in the United States. The number of red and white blood cell counts performed on a daily basis is much higher than this. Although the cost of each test is relatively small, the large number of tests performed make them a major item in the operation of the clinical laboratory.

The factors outlined above clearly indicate a strong need for automation of the analysis of formed elements of blood by an instrument system that not only accomplishes tests more efficiently than manual methods, but also measures important parameters directly with high precision and reliability. The latter consideration is of crucial importance in upgrading the clinical usefulness of the tests and in providing quantitative diagnostic parameters that are not currently available.

BRIEF STATEMENT OF THE INVENTION

Apparatus embodying the invention automatically identifies and analyzes cellular material by fluorescent staining and scanning by an automatically controlled microscope to extract distinguishing features from the cellular material. The apparatus is particularly useful in blood testing and automatically performs cell classification, counting and analysis. However, the techniques are applicable to the analysis of any other human or animal cellular material properly deposited on a microscope slide.

The technique, which is termed CytoDiagnostic Microscopic technique, (CDM) is attained through the computer controlled operation of a microscope in the examination of a slide containing cells previously stained with the fluorescent dyes. Morphological and chemical information are collected in this examination which permit determination of cell classification, maturation and anomaly. The cellular material is analyzed in a unique, automatic and high speed manner to provide analytic results not heretofore attainable through the use of conventional techniques and at speeds likewise not heretofore possible.

In one specific embodiment of the invention, means including a microscope are provided for detecting the presence of a fluorescent response to the exciting light. The detected fluorescence is employed to locate the site of the cellular material under investigation and to automatically focus the microscope. Scanning means scans the cellular material to determine form, size, texture, quantity and the like. This date yields information as to cell type, cell count, differential count and the like. The amount of data made available through the use of the system is significantly greater than that available through prior art techniques and the data is developed in a mere fraction of the time required by present day techniques and equipment.

An aspect of the invention is to provide a system that automatically performs a differential blood count by determining the type of white blood cells in a specimen under analysis through the use of the ratio of DNA and RNA present in the specimen.

OBJECTS OF THE INVENTION

It is therefore one object of the invention to provide a method for detecting and quantitatively analyzing the presence of constituents in cellular material through the use of fluorescent stains which specifically bind to said constituents and by exposing the cellular material to light of predetermined wavelengths to excite fluorescent responses of the stained material.

Another object of the invention is to provide an automatic system for analyzing the cellular material.

BRIEF DESCRIPTION OF THE DRAWINGS

The above, as well as other objects of the invention, will become apparent when reading the accompanying description and drawings, in which:

FIG. 1 is an illustration showing the development of blood cells.

FIG. 2 is a plan view showing the slide used in the analysis of a specimen.

FIG. 3 shows a plurality of curves relating the spectral response of fluorescently stained materials to particular exciting wavelengths, and is useful in describing the constituent detection technique of the present invention.

FIG. 4 is a block diagram showing a microscope system designed in accordance with the teachings of the present invention.

FIG. 4a is a filter wheel containing narrow band optical filters of appropriate and differing wavelengths.

FIG. 4b is a simplified perspective view of an image dissector tube employed in the system of FIG. 4.

FIG. 4c is a block diagram showing the computer interface of FIG. 4 in greater detail.

FIG. 5 is a plan view showing the relation between light spot size and search area of the dissector tube.

FIGS. 5a and 5b are plan views showing typical scanning patterns of the microscope system of FIG. 4.

FIG. 6 is a plan view of a cell and the technique employed to frame the cell.

FIG. 6a is a plan view of the searching pattern employed by the system of FIG. 4 for locating a detection point.

FIG. 7 is a flow diagram showing the steps performed by the system of FIG. 4 in the analysis of a blood sample.

FIG. 8 shows a curve showing the relation between DNA amplitude and Z position of the microscope stage and which is useful in explaining the microscope focusing technique of the present invention.

FIG. 9 is a schematic block diagram of a filter control circuit for use in the system of FIG. 4, FIG. 15 is a graphic representation of the dissection of a cell, FIG. 16 is a schematic block diagram of an A/D conversion circuit, and FIG. 17 is a graphic representation of the separation of cells attainable with a system embodying the invention.

GENERAL DESCRIPTION

Figure 10:
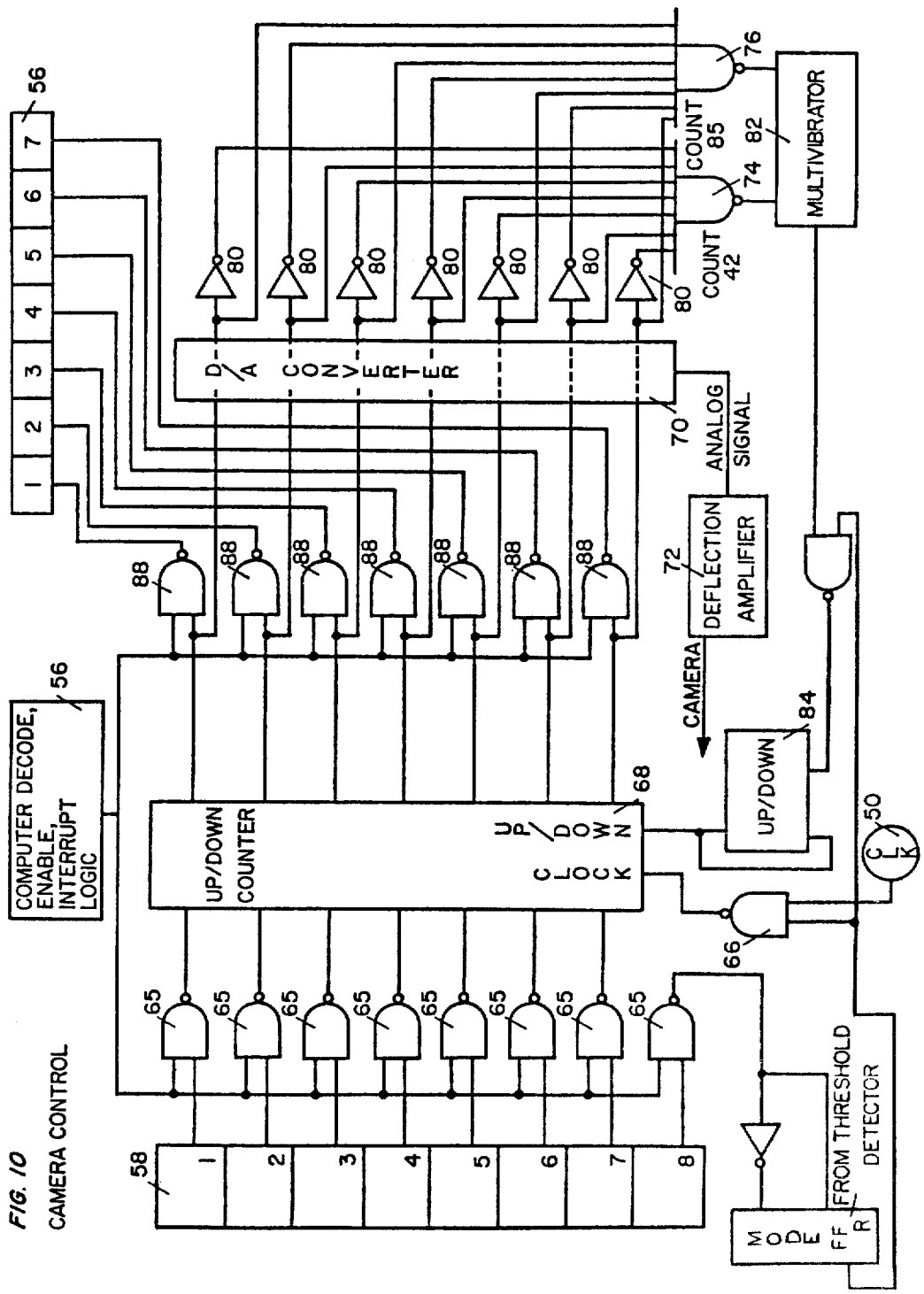
FIG. 10 is a schematic block diagram of a camera control circuit for use in the system of FIG. 4.

In order to automate the identification and counting of the various type cells in a biological sample, a method and system consisting of the following elements has been developed:

First, a standard volume of the biological sample is exposed to a standard volume of a mixture of a number (one or more) of stains. Each of these stains has the property of attaching itself to particular materials within a cell. Each of the stains has the further property that it will fluoresce. More particularly, the fluorescent property of the stain when bound with the cellular material is that of emitting light at distinctive wavelengths and amplitudes when illuminated by light which does not necessarily contain the emission wavelengths.

Second, a standard volume of material containing the stained cells is precipitated under the force of gravity, or by centrifugal force, onto a surface (i.e. slide) suitable for examination under a microscope.

Third, the cell-bearing surface is placed upon a transport which will enable said surface to be scanned, that is, examined point-by-point, by the microscope.

Fourth, as the surface is being scanned by the microscope, the field of view of the microscope on the surface containing the cells is illuminated through the microscope objective which also acts as a condenser lens; this is a preferred method; however transmission optics will also serve. The optical system and the surface itself are designed so that little of the illumination is reflected back into the microscope. However, any fluorescent light originating in the stained cell material will be picked up and imaged by the microscope.

Fifth, the fluorescent light, whose wavelength and amplitude depends upon the stain and cell materials from which it originated, is subjected to a selected one of a number of filters before being imaged by the microscope. Each of these filters is designed to pass only the wavelengths which are characteristic of one of the aforementioned stain/cellular material combinations. Thus, each filter serves to identify a particular cell type or cell material type.

Sixth, the light imaged by the microscope is projected onto a photoelectric transducer or camera such as an image dissector, vidicon, or the like. The camera serves not only to detect the presence and amount of light being imaged by the microscope but also to convert information as to the form of the image into electrical signals.

Seventh, the output of the camera is amplified, converted into digital form and analyzed by a digital computer. The digital computer serves also to (1) control the motion of the transport to effect a scan of the examining surface so as to detect the presence of a cell within the illuminated area as well as to arrest the motion to permit examination of particular cells, (2) select which of the filters is to be used at any time, (3) focus the microscope, (4) determine the type of individual cells on the basis of the fluorescent response, size, number of lobes, shape and texture, whichever are needed, (5) make a count of cell types, (6) prepare a report on such factors as the identity of the patient and the results of the analysis.

Blood testing requirements can be most easily understood on the basis of the normal origin and development of the cells of the blood. These include red blood cells (RBC), platelets (or thrombocytes), and white blood cells (WBC) which are subdivided into mononuclear cells, lymphocytes and polymorphonuclear (PMN) leukocytes. The PMN are further divided into neutrophils, eosinophils and basophils. FIG. 1 illustrates the development (maturation) of blood cells. Normally only mature cells, shown below the double line DL, are found in blood. The presence of immature cells is most often indicative of a serious hematologic disorder, such as leukemia. A review of FIG. 1 leads inevitably to the conclusion that the correct identification of cells along each of the vertical maturation pathways is complex due to the extremely close resemblance of adjacent phases of development and requires high quality data.

A suitable method of preparation of a blood cell specimen is of paramount importance in the development of a practical clinical laboratory system. The techniques utilized by the CDM fall within the normal range of laboratory procedures and yet provide the uniform rendering of cell characteristics required to support the multiparametric analysis (size, shape, content) of the formed elements of the blood.

SPECIMEN PREPARATION - GENERAL

The specimen preparation procedure is designed to support the operation of the automated microscope in the classification, analysis and counting of the formed elements of the blood. It is particularly optimized to enhance the capabilities of the CDM system which utilizes fluorescence and absorbance techniques. The requirements placed on specimen preparation for this advanced automated microscope system may be summarized as follows:

1. The details of component features of cells should be enhanced through differential staining to provide and facilitate:
   a. simplified automated procedures for locating cell types of interest.
   b. the analysis of internal cell organelles through the enhancement of particular features at the expense of features which are not of immediate interest.
   c. automatic focusing on the cell through the provision of sharp, bright structures for focusing upon.
   d. the quantization of the amount of materials (eg: DNA, RNA, Hemoglobin) of various types in the cell.
2. Stains must be quantitatively absorbed by viable cells to permit standardized and repeatable analytic results. Quantitative absorption is attained and enhanced through mixing the stains with a buffering system and applying these to live blood cells.
3. After the stains have been quantitatively incorporated by the critical constituents of the viable cells and the cells are fixed, stain-cell material relationships must be maintained for long periods of time. DNA and RNA stabilizers must be provided within the mixture to effect the long term binding of dyes and cell components.
4. Cells of all types within the specimen must be uniformly spread on the surface of the slide for examination by the microscope. The following factors must be considered in preparing the slide:
   a. cells of each type within the specimen must be uniformly distributed over the examining area to provide cell distributions which are faithfully proportionate to the white cell count, the platelet count, the red cell count and the hematocrit of the specimen.
   b. each cell must be symmetrically spread to properly display its features thus facilitating morphologic analysis (eg: polymorphonuclear cell lobes must not overlap).
5. An examining surface/slide should be provided which has proper characteristics for optimizing:
   a. automatic insertion into the microscope
   b. automatic specimen identification
   c. suitable and uniform spreading of cells
   d. surface characteristics which support automated analysis via fluorescence or absorbance.
6. A device which will uniformly and proportionally spread a measured amount of specimen and stains, etc. upon the examining surface.
7. Means for measuring specimen, stains, etc. for mixing these and for emplacing proper amounts on an examining surface.

Specimen preparation begins with the collection of a small amount of whole venous blood obtained through use of any of the currently employed clinical techniques. Blood may for example be extracted from an arm via a hypodermic needle in a hospital ward. The sample is inserted into a test tube and an instruction sheet including patient identification, tests required, etc. is filled out. The test tube may be a vaccutainer ® or other similar device. At this time a measured portion of the sample should be mixed with a measured quantity of an anticoagulant such as versene buffer anticoagulant. In one preferred mode of operation the test tube will have the anticoagulant prestored within it prior to the insertion of blood. The sample whether refrigerated or stored at room temperature will be acceptable for further processing for several hours after collection.

When the sample arrives at the laboratory it is equilibrated by rocking to assure a homogeneous mixture and a precisely measured aliquot (approximately 0.01 ML) is removed by a micropipette. The contents of the micropipette are then mixed with a precise amount (approximately 5 ML) of a Stain-Diluent-Stabilizer (SDS) mixture. The SDS/blood mixture is equilibrated and allowed to stand at room temperature for several minutes to permit the formed elements of the blood to take up the stains. After the SDS/blood mixture is accomplished the specimen may be stored under refrigeration for weeks and will maintain its adequacy for automated analysis.

At a convenient time, an accurately measured amount of SDS/blood is removed from its mixing container through use of a micropipette and is dropped on the examining surface of a slide for spreading. One type of device which will provide uniform, repeatable cell distribution over the surface of a slide is a hematologic spinner. Spinners which may be utilized to perform this task are manufactured by the Shandon Instrument Company. Accelerations and velocities are carefully controlled by all of the above spinners which will spread a specimen in 0.5 to 2 seconds as a function of the volume and viscosity of the mixture.

When spinning is complete the specimen must be fixed to kill the white cells or they will begin to "crawl" and distort their morphological image. Fixing may be done in a number of ways. One adequate and preferred procedure is to fix the specimen through drying it via an air stream immediately upon the completion of spinning. When prepared in this manner (ie: using the SDS containing DNA and RNA stabilizers) the slide may be stored for extended periods of time prior to and subsequent to analysis.

The slide thus prepared has had emplaced upon it (during the manufacturing process) equivalent man and machine readable identifying marks. An operator may enter the identifying characters found on the slide into the automated microscope. Additionally he may enter pertinent data (patient I.D. etc) found on the instruction sheet. The slide is then inserted into the automated microscope for analysis. The microscope can associate the particular slide, as identified by the machine readable marks, with the slide identification characters entered by the operator. Other information entered by the operator is then associated with the slide identification and, subsequently, with the results of the specimen analysis.

THE STAIN-DILUENT-STABILIZER (SDS)

The SDS mixture is designed to provide reliable and repeatable test results in the preparation of live cell specimens in the normal clinical laboratory environment. It is a uniform solution containing precise quantities of fluorescing stain(s), nucleic acid stabilizers, buffers and an agent designed to adjust the viscosity of the SDS/blood mixture. Combinations of fluorescent stains may be utilized in the mix. These stains specifically and quantitatively bind to cell constituents of interest and, when properly illuminated provide fluorescing light outputs whose wavelength and amplitude are a function of the type and amount of material stained. FIG. 3 is an example of stain binding and response. It illustrates the fluorescing characteristics of white blood cells when these are appropriately stained with materials of the acridine orange family. When narrow band illumination (here shown centered at 465 nanometers) is applied to such cells they will fluoresce according to the fluorescent characteristic spectra shown in FIG. 3, nuclear material (whose amplitude is a function of the packing characteristics of the helical structure of the DNA of the cell type) will have a green fluorescent peak, in the area of 530NM. Cytoplasmic material (primarily RNA although also including significant quantities of other materials in a manner characteristic of the cell type) will have a red fluorescent peak in the area of 630 NM.

Experiments conducted during the development of the staining procedure have lead to the discovery that the ratio of composite white cell DNA/RNA fluorescent response may be used to accurately identify the type of white cell being examined.

A further useful feature of the fluorescent staining employed is that binding to hemoglobin or red cell membranes does not occur. Thus red cells will not fluoresce and will be ignored by an automated microscope operating on white cells. This characteristic permits the microscope to operate at high speeds in white cell analysis (there are approximately 5,000 red cells to each white cell in normal blood and these will not be seen during white cell search and analysis). Red cell hemoglobin analysis is performed through absorption on a mirrored portion of the slide surface.

The small proportion of immature red cells which contain RNA (reticulcytes) fluoresce and may be analyzed for maturity by testing the composite RNA response. These cannot be confused with white cells which contain green fluorescing nuclei and no hemoglobin. Additionally, they cannot be confused with platelets which are smaller, have granular structures and which fluoresce at different composite amplitudes. Platelets do not have nuclei and will not be detected in a white cell search for green nuclear material.

The detailed morphologic analysis of the white cell through electro-optical techniques employing an electronically controlled TV-like camera is greatly enhanced by the use of fluorescence. The nucleus can be examined with no interference by cytoplasmic material if a green filter is placed before the camera tube. Similarly red fluorescing cytoplasm can be examined with no interference by nuclear material. Further, such measurements are not densitometric. Granules appear bright and sharp within the cytoplasm. Nuclear features (lobes, nucleoli, etc.) are bright and have sharp and crisp edges. These factors very significantly improve the signal-to-noise and resolution at which data may be taken.

The fact that the fluorescing material appears as a bright source of light to the microscope/camera permits simple and accurate focusing procedures to be employed. The microscope system provides a fixed examination of a bright point on the cell and moves the stage up and down to maximize the light response. When the camera or transducer reading is maximized, the system is in best focus.

As the nuclear and cytoplasmic point by point amplitude readings for a cell are taken they are summed. These summations can, as previously stated, be utilized to determine cell type. It is clear that the accuracy of the summations is significantly enhanced through the use of fluorescent binding characteristics. Densitometric measurements heretofore provided summations of the combined amount of nuclear and cytoplasmic materials found in a reading point area and not of separate DNA or RNA constituents.

A variety of stains will bind with cellular material and will fluoresce. One of a selection including ethidium bromide, metonil yellow or eosin Y may be used, and is preferred. Other stains include Brilliant sulfaflavin, Rose Bengal, Aurophosphine Acriflavine, Rhodamine B, Fast Green, Pyronin Y and Methyl Green. A preferred family of stains includes acridine orange and corophasphine R. The spectral responses of white cells shown in FIG. 3 are derived from the use of acridine orange.

One preferred usage combines acridine orange and corophasphine R. The optimum proportion of combined stain to blood is approximately $10^{-3}$ Molar. The fluorescene characteristics of blood cells are altered by the proportion of the two dyes; however, for a given proportion uniform results are obtained.

A buffering system is provided in the SDS to enhance the capability of live cells to quantitatively absorb the stains in a repeatable manner. The buffering system maintains stain/blood Ph and osmolarity within optimal limits and improves the capability of cells and their organelles to quantitatively absorb stains while maintaining their viability and integrity. One diluant which has proven acceptable is $Ca^{++}$, $Mg^{++}$ free phosphate buffered saline. Alternative buffers such as HEPES will also be acceptable.

Stabilizers which maintain the quantitative relationships of stains and cell materials for extended periods after the specimen is fixed on the slide are provided within the SDS mixture. These include a $DNA^1$ se inhibitor and an $RNA^1$ se inhibitor each in $10^{-3}$ to $10^{-5}$ molar quantities. The inhibitors preferred are adenosine 3'5' diphosphate and thymidine 3'5' diphosphate although a variety of ribo and deoxyribo dinucletides may also be employed.

The SDS incorporates a viscosity medium whose function is to provide proper distribution of cells on a slide after spinning.

CDM system performs counts of the various types of cells in a blood specimen through examining a fixed area of the specimen slide surface, counting the cells of each category detected therein and extrapolating these counts to the proportions of each cell type and the absolute count (per unit volume) of each cell type contained in the specimen. Alternatively a fixed number of cells can be counted and the values extrapolated from the area examined. For a specimen prepared in the manner described herein, the cells are uniformly spread in a manner which is accurately proportionate to the red cell count, the differential white cell count, the white cell count and the hematrocrit. The accuracy of the distribution is not appreciably affected by cell specific gravity, abnormalities in cell size or shape or by the hematrocrit (within limits compatible with human life) of the specimen.

When a satisfactory viscosity medium is utilized great accuracy can be obtained in performing counts. Table I was derived through an empirical experiment with the following steps:

1. A blood specimen was centrifuged and the serum was removed.
2. The blood (essentially the red blood cells remaining) was mixed with an amount of serum minimal to sustain life.
3. A measured amount of SDS was mixed with the specimen.
4. The specimen was spun onto a cleaned glass examining surface by a Perkin Elmer Spinner set to two seconds of spin at 6,000 RPM.
5. The slide was examined under a microscope and red blood cells were counted in 24 grid areas each 200×200 microns on a side.
6. The above was repeated for a normal and very high serum to cell ratio.

Table I

| | Cell Distribution Slide Summary | | | | |
|---|---|---|---|---|---|
| | | | No. of Red Cells To Be Counted for 95% Confidence of Less Than Indicated Error in Ave. No. of Red Cells per Unit Volume | | |
| Slide No. | Ave. No. of RBC per Field (m) | Variance of RBC per Field $(o^2)$ | 5% Error | 2% Error | 1% Error |
| 1 | 86.35 | 8.39 | 155 | 972 | 3887 |
| 2 | 90.60 | 8.61 | 152 | 950 | 3801 |
| 3 | 89.95 | 7.67 | 136 | 853 | 3411 |
| 4 | 87.05 | 10.11 | 186 | 1161 | 4646 |
| 5 | 86.10 | 9.61 | 179 | 1116 | 4465 |
| 6 | 82.85 | 13.47 | 260 | 1586 | 6503 |

Table I indicates the results obtained for six (6) different slides. The number of red cells are shown which need to be counted in order to achieve a 95% confidence of less than the indicated error in the measurement of the average number of red cells per unit volume. The average number and variance of the number of red blood cells are based upon counting the number of cells in each of 24 grid areas. The number of red cells to be counted are determined as follows:

$$\text{No. of red cells} = (Xo'/o')^2/m$$

where m is the sample mean, $o^2$, is the sample variance, X is the number of standard deviations (assuming a normal distribution of errors) which corresponds to the desired confidence level, and 2 is the allowable error (measured as a decimal).

The viscosity agent used in the foregoing experiment is FICOLL (Pharmacia Fine Chemicals) in a 20–30% weight to volume mixture. The viscosity agent can be any long-chain inert water-soluble polysaccharide including dextraiy and polyethylene glycole. The concentration required in the SDS mix is derived empirically according to the system parameters such as:

. slide surface wettability
. spinner acceleration
. spinner speed
. spinning time
. automatic microscope design In summary, the SDS mixture is a composite of fluorescent stains, buffers, stabilizers and viscosity media which are combined in precise amounts to achieve, within a single mixture, the ability to specifically stain and stabilize cell components and to distribute blood cells uniformly and proportionately over an appropriate slide surface. This single mixture, in combination with CDM automatic mixroscope will permit all common tests of the formed elements of the blood to be performed on a single preparation.

THE SLIDE

The examining surface (slide or microslide) bears the specimen to be analyzed by the automated microscope. As described previously, the preferred method of specimen preparation is to spin the blood/SDS mixture onto a slide surface so as to assure that blood cells are spread proportionately and uniformly over the surface and that individual cell characteristics are properly displayed. The features of the examining surface which are of significance in the design of the slide include dimension, surface character, reflectivity, means for identifying the specimen and a geometric configuration suitable for automatically inserting the slide into the automated microscope.

FIG. 2 illustrates a slide configuration optimized for use with the CDM. THE EXAMINING SURFACE An optimum mode for examining red cells is through an analysis of the degradation of the light passing through the cell by the hemoglobin content of the cell. Light, particularly light at the peak absorption wave length of hemoglobin (approx. 408 Nanometers) is absorbed uniformly by the hemoglobin of the cell, as a function of the distance the light traverses in the cell. Using this information and the automated procedures inherent in the CDM design, values can be obtained which are proportional to the area and volume of a red cell and to its hemoglobin content.

Two methods of measuring the absorbance of a red cell fixed on a slide are apparent. In the first, the common technique wherein light is transmitted through the bottom of a transparent slide, through the red cell and to a measuring system may be used. A Variation of the system reverses the position of the light source and the measuring system.

This method has disadvantages in practice due to difficulties encountered in optical alignment and in the distortions which occur when the light passes through the slide. These problems are of little significance in manual examination but they are important when detailed analysis of the cell by an automated microscope is to be performed. Such automated analysis includes a dense, point by point (each point a small fraction of the cell area) examination for purposes of quantitative and morphologic data collection. It has been found that for purposes of improving data accuracy and reducing system production costs a method of examination via the double absorbance of light is of significant advantage.

Double absorption is obtained through the use of the novel slide of the present invention. Red cell examination is performed on a reflective portion of the examining surface which has been prepared as described previously. Light of the appropriate wavelength is directed through the microscope objective lens to the specimen. This light passes through a red cell, impinges on the reflective slide surface and passes through the red cell again so that a double absorption of light of the appropriate wavelength is obtained prior to the unabsorbed light being received by the objective lens. The double absorption technique very significantly increases the accuracy of a reading by the microscope. Further, it eliminates the distortions of light passing through the slide which are inherent in a transmitted light system. No distortion is introduced into readings obtained in the slide of the present invention since optically flat reflective surfaces are well within the state of the art. Use of this technique also eliminates the requirement for an illuminating lens and associated alignment procedures.

A reflective area is not required in the slide surface portion in which white cells and platelets are to be examined. These cells bind stain and fluoresce when appropriately illuminated and are examined through uses of emitted light. At the illuminating wavelengths utilized for hemoglobin analysis white cells and platelets do not absorb to any significant degree. For example, white cells are effectively transparent to light at 408 NM and are not seen during red cell analysis. Similarly red cells do not significantly absorb light in the 465 NM range and are not visible during white cell analysis.

The amount of surface reflectivity required for red cell analysis in the mirrored area of the slide is a function of the intensity of illumination applied, the absorption characteristic of the microscope filters and the sensitivity of the reading (camera) means. In one implementation, an approximately 5% reflective surface is adequate. A first surface mirror with a dense fine grain reflective coating is desirable. One method of obtaining this is through use of a first surface evaporated aluminum coating. A preferred technique incorporates reflective mylar tape applied to the slide surface.

Note that uniformity and not absolute control of reflectivity is required. This proves satisfactory because the technique employed by the CDM is relative, comparing the degraded light passing through a red cell with the average reflectivity of surrounding areas not containing cells. FIG. 4 illustrates the double absorption technique.

FIG. 2 illustrates one possible slide configuration. The surface includes a reflective area for the analysis of red cells and their hemoglobin content. A non-reflective area is included for the examination of cells which are analyzed through fluorescence. As described earlier, a measured amount of specimen is emplaced and spread on the examining surface through spinning.

The dimensions of the surface are not critical except in that the area must be adequate to contain sufficient cells for a complete blood count (CBC). To accord with existing practice and storage media the size chosen is the same as that of a conventional microslide, according to international standard, (i.e.: 0.07 × 1 × 3 inches), with the slide materials being of glass (refractive index 1.3) or plastic. The material chosen must be relatively flat, dimensionally stable non fluorescent and have surface characteristics (wettability, etc.) which promote the proper distribution of cells via spinning. Materials which have proven adequate are glass, mylar, and acrylic plastics. The use of plastic type materials is attractive due to cost considerations. Plastics are more practical in this slide application than in others because light transmission through the slide is not required and thus the poor optical characteristics of plastic are unimportant.

Several features may be incorporated in the slide design to enhance its utility in automated applications. These are as follows:

1. One corner of the slide is cut off to assure that it is always inserted into the microscope in the same manner. This is important in re-locating cells found in earlier examinations, in properly positioning the reflective area and in properly orienting the slide so that the automated microscope can interpret the slide identification characters.
2. Machine readable characters (analogous to paper tapes or mark-sense bits) are placed on the slide so that the microscope system can read the slide number. This number is assigned and emplaced upon the slide during the manufacturing process. A label may be attached to the bottom or one end of the slide which includes commensurate man and machine readable numbers, as shown in FIG. 2. The machine readable characters are placed upon a background which is in substantial color contrasts to the inks utilized. The range of numbers chosen for imprinting should be substantial to minimize the probability of having two slides of the same identification number concurrently in a laboratory. As described earlier, the operator will enter (via keyboard, card, etc.) the man readable numbers into the microscope system and append pertinent data (patient identification, etc.). When the slide is inserted, the microscope will read the machine readable characters and associate these with the operator data and, with automated checking, minimize the possibility of mixing specimens.
3. The cross section of the slide 30 is a modified 'I' beam, not shown. This configuration has several advantages.
    a. slides may easily be placed in a stable, self stacking pile.
    b. specimen surfaces are separated by the gap from the slide above and will not be scraped by it.
    c. automated microscope entry and exit from and to hoppers are simplified for the operator and the machine.
    d. the rigidity and stability of the slide are enhanced by its rails and the amount of material employed may thus be reduced.

When the blood specimen is prepared as described and the microslide 30 is placed on the microscope stage and white blood cells are illuminated by monochromatic light in the blue-green region they will fluoresce as shown by the family of curves in FIG. 3. A fluorescent response in the green region (530 NM) indicates the presence of DNA (nuclear) related materials. A response in the red region (630 NM) indicates the presence of RNA (cytoplasma) related materials. Note that exciting and examining frequencies need not be precisely determined, however once selected they must be maintained for repeatability of results.

DETAILED DESCRIPTION

The biological sample is examined automatically by the equipment illustrated in FIG. 4. The biological slide 30 is mounted onto a microscope stage 2 which is capable of movement in three orthogonal directions; x, y and z. Bidirectional motors 3, 4 and 5 provide the aforementioned direction of motion under the control of computer 7. Specifically, motors 3, 4 and 5 are controlled through interface 6 under control of the computer 7. A number of small computers may be utilized as the controller in the CDM. Among them are the PDP-8, PDP-11 (Digital Equipment Corporation, DEC), Nova 800, Nova 1200 (Data General), EPI 118 (Electronic Processors Inc.). In this description, the PDP-8 computer is the computer selected. Methods of creating interfaces between the PDP-8 and peripheral equipments are described in various DEC manuals and documents. Equipment literature describes, for example, interfaces with cathode ray tubes, phototubes, teletypes, A/D converters, D/A converters, stepper motors, etc. The DEC equipment literature includes the Small Computer Handbook (1967, 1968) and the Digital Logic Handbooks of the same period.

Methods of programming the PDP-8 are provided in the DEC Small Computer Handbook (1967) and in the DEC Introduction to Programming (1969) manuals. DEC also has a users association (DECUS) whose primary function is to allow users of their equipment to trade operating programs. In the above pregramming literature are descriptions of techniques for the programming control of A/Ds, D/As, and motors; routines that control CTRs and teletypes, routines that solve geometric problems, that read pictures via TV cameras, that prepare histograms, etc. It is important to note that the program per se would vary from computer to computer as selected and hence is not the invention per se.

The following sections include interface and control logic diagrams. For example, blocks are shown and described as Computer Decode, Enable, Interrupt, Logic. All digital computers have such logic which is generally similar to the logic of other such computers. Therefore, as manufacturers describe appropriate utilization techniques in their literature, these are considered to be well within the knowledge of a person skilled in the art. The logic that is shown may be constructed from circuits provided by several manufacturers. For example, modules marketed by DEC as described in the Digital Logic Handbook (1967) and including Logic and A/D, D/A circuitry are applicable. A preferred implementation is for motors 3, 4 and 5 to be of the electrical ratchet type commonly referred to as stepping motors.

The particular area on the biological slide under examination at any instant is illuminated by monochromatic light designated by dotted line 12. The monochromatic light 12 is obtained by a bright light source 8 and monochromator 9. A xenon lamp, the preferred source, provides a very broad frequency highly intense light beam from a limited source area.

In one implementation particularly useful in research applications, the monochromator is of the grating type which accepts the broad band light from the source, refracts it, and provides a narrow band of monochromatic light selected by the monochromator slit. In an alternate version preferred for clinical laboratory applications, the monochromator is a filter wheel 20 as shown in FIG. 4a, containing narrow band optical filters 20a of proper and differing wavelengths. In either monochromator implementation the proper exciting wavelength of light is provided through use of step motor 9a controlled through interface 6 by computer 7. The monochromatic light is reflected by dichroic mirror 10, through the microscope condenser/objective lens 11 onto the spot on the biological slide 30 under examination.

In performing the detection of red cell hemoglobin, for example, the degradation of light absorbed by the cell as opposed to the light reflected from regions adjacent to and not containing the cell is measured. Sufficient light is transmitted through mirror 10 to permit the test.

Focusing is accomplished with motor 5 through interface 6 under control of computer 7. The motor 5 moves the stage 2 carrying slide 1 in relation to the microscope lens 11 (i.e. vertically up or down) for purposes of focusing. The microscope objective lens 11 acts as a condenser for the monochromatic light beam 12 prior to its incidence on the biological slide 1 and as a microscope objective lens for the fluorescent light emitted by the cellular material under examination. The emitted fluorescent light from the material under examination passes, in succession, through the microscope objective lens 11, the dichromatic mirror 10, the barrier (eyepiece) lens 13, the barrier filter 14 and onto the camera 16. The barrier filter successively selects the fluorescent light wavelengths to be examined. The barrier filter 14 contains narrow band optical filtersters of selected wavelengths and may be of a construction similar to the filter wheel 20 of FIG. 4a. A particular barrier filter may be indexed by motor 15 controlled through interface 6 of computer 7.

The first step in the process, in one preferred embodiment, is to search for the presence of white blood cells. FIG. 7 illustrates the steps or overall flow chart of the method of system operation. The cell bearing surface to be examined is mounted on the stage (6.1) and brought into focus through maximizing the light energy response of the reflective area of the slide. The computer system is initialized for white cell counting (6.2) and filters are set for detection of nuclear DNA (6.3). Search is initiated with stage and camera scanning motion. When a threshold detection, denoting the presence of DNA, occurs, the stage and camera scans cease and the computer centers (frames), refocuses and analyzes the nucleus (6.4). Since the reading spot is approximately 0.7 microns and the largest cell approximately 20 microns less than 3,000 words of memory of the computer 7 are required to store the nuclear and cytoplasmic data for a white cell.

After the nucleus is analyzed the filters are switched to read RNA, the cytoplasm is framed, focused and analyzed (6.5). A ratio is then determined of the amount of RNA to DNA (nuclear/cytoplasmic material) (6.6).

The result of this computation determines the type of white cell under analysis. Further computations permit the cell to be "binned" or classified according to its maturation or normal/abnormal characteristics. These computations utilize such data as lobe count, amplitude histograms (distribution of chromatic material), presence of nucleoli, nuclear and cytoplasmic areas, shape, compactness, etc.

When the appropriate cell type bin is incremented a test is made to determine whether enough white cells have been counted (6.7). If an insufficient number have been counted search begins for another white cell. If the count is sufficient, the white cell count is made through a computation relating the count to the search area traversed to the blood dilution (6.8).

When the white cell is completed the computer sets its conditions for red cell counting (6.9). The hemoglobin absorption filters are set (6.10) and stage motion is initiated in the reflective slide area with the camera search position centered and stationary. Motion is continued for a specific distance and all red cells encountered are detected by the threshold detector and counted by the computer. The red cell count is taken through a computation relating the count to the search area to the blood dilution (6.11).

After the red cell count is made, red cell analysis takes place. A red cell is located in the illuminated area and dissected for hemoglobin (6.12). Thereafter, filters are switched to RNA and the cell is dissected again (6.13) to determine whether it is a reticulocyte. The cell is analyzed and binned (6.14) using information on size, hemoglobin, RNA, shape, etc. The hemoglobin filters are switched in (6.15) and a test is made to determine whether sufficient red cells have been counted (6.16). If not, the stage is moved and new red cells are analyzed. When red cell counting is finished the mean corpuscular volume is computed as is the hematocrit (proportion of red cells in a volume of blood specimen) and platelet analysis is initiated (6.18).

The computer sets the system for platelet search (6.19) and selects the RNA filters (6.20). A number of platelets are counted through threshold detection in the search mode. Use of the count, information on the area traversed and the known dilution of the specimen permits a platelet count (6.21) to be made. Thereafter a number of platelets are analyzed for RNA (6.22) andand size. When a sufficient number have been analyzed (6.23) the total blood test is completed and results are printed (6.24).

In more detail, in the search for the presence of white blood cells or platelets, the correct exciting and reading wavelengths of light are selected through monochromator 9 and barrier filter 14 for the detection of the particular cell type and cellular material to be analyzed. FIG. 9 illustrates the control and activation mechanisms of the filter wheels as shown in FIGS. 4, 4A and 4C. The filter wheel 20 is moved by a stepper motor 9 under control of a translator module 40.

One stepper motor/translator module combination which will provide satisfactory results is manufactured by the Superior Electric Company. The motor is a SLO-SYN model HS5OL and the translator module is the ST1800B as described in Catalog SS1265-3 issued in 1967. This combination is capable of rotating the filter wheel 20 at a rate of several hundred 1.8 degree steps per second. Inputs to the translator module are a direction-of-rotation via level 42, and step pulses via 44. During operations, the directional level is held in a flip-flop 46, and step pulses are provided via a clock gate 48. The clock 50 is free-running and is pre-set to provide pulses at a desired rate to the gate 48. When the gate 48 is enabled by the flip-flop 52 step pulses will be provided to the translator module 40 and the stepper motor 9. An up/down counter 54 made up of two four bit circuits is pre-set by the computer to enable an appropriate number of 1.8 degree motor positioning steps to occur. When the computer has set the counter 54 the direction flip-flop 46 and the clock enable flip-flop 52 stepping of the counter 54 and filter wheel 20 begins. For each clock pulse the counter 54 and motor 9 each take one step. When the counter 54 reaches a terminal step it provides a reset signal to the clock enable flip-flop 52 and a signal to the computer 7 via interrupt logic 56. The clock enable flip-flop 52 output changes state and disables the clock gate 48 inhibiting count pulses to the counter 54 and step pulses to the translator module 40, motor 9 and filter wheel 20.

A preset table stored in the memory 55 of the computer 7 provides the filter number. The memory 55 table contains a motor step number for each filter position on the illuminating and barrier filter wheels and looks up the motor position for the filter selected. The present position of the filter wheel is, after a once per day start-up initialization, always maintained and updated in the computer 7. Present position is subtracted from the desired position. The result of this operation provides a direction of motion (if negative to a lower number step, if positive to a higher number step) and a count of steps which is applied to the motor module 40. Accumulator 58 is an illustration of some of the accumulator bit positions of a computer such as a PDP-8.

A step count is placed in the first eight locations of the accumulator 58. Eight bits are sufficient as they provide 256 possible steps and a full rotation of the filter wheel 20 requires 200 steps of 1.8 degrees each. A direction bit in position 9 of the accumulator 58 and an enable bit is placed in position 10. The values in the accumulator are then transferred into the counter 54 and the enable 52 and direction flip-flops are set.

Setting the enable flip-flop 52 permits clock pulses 44 to reach and step the motor 9 and filter wheel 20 in the direction specified by the direction flip-flop 46. When the counter 54 reaches a terminal value, it provides a reset signal to the enable flip-flop 52 which prevents clock pulses from stepping the filter wheel 20 and counter 54. Additionally, the terminal value provides a signal to the computer via the interrupt logic 56 which indicates that the selected filter is in position.

Referring back to FIG. 4, concurrent operation of the stage 2 and the camera 16 create a raster scan pattern trace on the biological slide. FIG. 5 shows the light spot (LS) formed on the surface 16a of the camera 16. It should be understood that the spot (LS) is greatly enlarged in the figure for purposes of simplicity. The spot diameter is typically of the order of 0.004 inches. Arrow A designates the stage motion during the search. Arrows B and C designate the alternating trace motions of the strokes. A repetitive one dimensional scan pattern is created on the camera 16 under control of computer 7 through the x or y deflection amplifier 17, Digital to analog converter 18 and interface 6. At the same time, the stage is moved in a path that is orthogonal to the scan pattern. The combined camera search/stage motion patterns lead to a search trace similar to that shown in FIG. 5a or FIG. 5b. The combined effects of the traces B and C together with stage movement A develop the traces as shown. Note that the camera trace/stage motion timings are selected so that any cell searched for will be "seen" by the system and not pass between strokes.

An extended description of the mechanization of the white cell and platelet search mode is illustrated in FIG. 10. FIG. 10 further illustrates the interface shown in FIG. 4C which is used to control one axis of the camera reading position. The logic for the control of the second axis is similar. A representation of 8 computer accumulator bit position is shown by 58. To initiate stroking bits are set into stages 7 and 8 of the accumulator and an execute instruction is given via computer control logic 56.

The camera 16, x-y deflection amplifiers 17 and D/A converters 18 (FIG. 4) are such that the camera reading (illuminated) area can be examined to one part in 128 in x and in y directions. This provides a range of over sixteen thousand points which may be individually examined. In search the middle third of the light spot is to be examined. A setting of bit 7 in the accumulator 58 by the computer, representing a count of 64, will initially position the camera 16 to a central value for the start of search. Setting bit 8 in the accumulator 58 places the system into automatic search via the mode flip-flop 64. The automatic mode output of flip-flop 64 enables gate 66 and permits clock pulses to reach and step the up/down counter 68. Outputs of this counter are passed to the x or y D/A converter 70. The resulting D/A analog output is transmitted to the deflection amplifier 72 and to the camera deflection circuitry (FIG. 4b) which moves the electron image point selected to the camera aperture reading position. Each clock pulse passed to the up/down counter 68 via the gate 66 causes the counter to step and the effective reading position to change.

The 'present' setting of the counter is also transmitted to two nand gates 74 and 76. Prior to reaching lower gate 74 bits 1, 3, 5, and 7 are inverted in inverters 80. Thus the nand gate will actuate when 1, 3, 5, and 7 are not set and 2, 4 and 7 are set providing an output when the counter is exactly 42. Similarly, the upper gate 76 will actuate when 2, 4 and 6 are not set and 1, 3, 5 and 7 are set, providing an output when the count is exactly 85. Note that counts of 42 and 85 represent distances of approximately 30 and 60 microns across the 90 micron spot when using a 0.7 micron reading aperture and search occurs between these positions. When a count of 42 or 85 is attained the multivibrator 82 is triggered and the state of the up/down flip-flop 84 is changed. When this occurs the direction of counter 68 stepping is reversed and the direction of stroking is reversed until the counter reaches 42 or 85 again. Tradeoffs on deflection yoke characteristics and on signal-to-noise based on camera, amplifier, etc. characteristics, indicate that an appropriate rate is approximately three microseconds. This yields a single stroke (FIGS. 5B and 5C) time of approximately 130 microseconds for 44 steps.

When the threshold amplifier 21 of FIG. 4 detects a sufficient signal amplitude thereby denoting a WBC nuclear detection, it passes a pulse to the mode flip-flop 64 which causes the flip-flop 64 to reset. This disables clock gate 66 and inhibits stepping and freezes the reading position of the camera. The detection position is read by the computer 7 via control logic 56, counter 68 and drivers 88.

Figure 11:
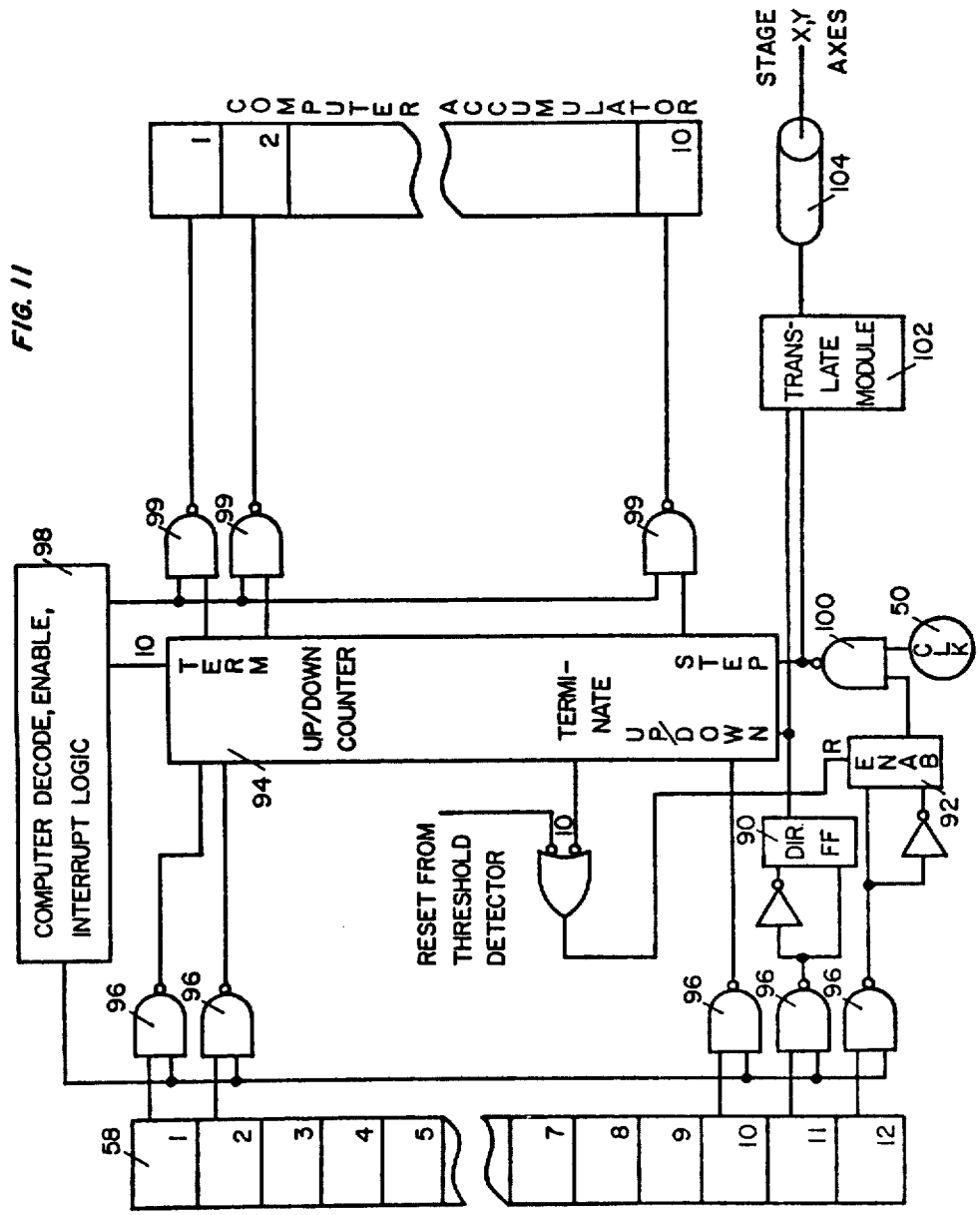
FIG. 11 is a schematic block diagram of a stage control circuit for use in the system of FIG. 4.

The stage 2 is activated to move during the search mode after stroking is initiated. Interface logic illustrated in FIGS. 4C and 11 shows the mechanization needed to move the x or y stage. Activation begins when the count of the number of steps desired is transferred into the low order bits of the computer accumulator 58. Additionally a direction bit is set in flip-flop 90 and an enable bit is set in flip-flop 92. The setting of the enable flip-flop 92 and the counter 94 via drivers 96 and control logic 98 permits clock pulses to pass through a gate 100. These pulses step the counter 94 in the direction specified by the direction flip-flop 90. Additionally, the clock pulses and direction level are passed to the translate module 102 and thence to the motor 104 and the stage 2. The translate module 102 and the motor 104 are similar to those described earlier for filter motion.

The start of search is at a stage initial position at an extreme end of the central non-reflective slide area which contains the specimen. The interface counter 94 is set to a preset position as determined by the stored program in the computer memory 55 and motion is initiated in a direction into the specimen. Approximately 500 steps (0.5 inches at 20 microns per step) are taken after which the counter 94 is terminated thereby disabling clock pulses from the clock 106 and interrupting the computer logic 108. The computer then updates an area traversed summation. This process is continued until a programmed cell count threshold or a sufficient area is traversed. When the search termination occurs the cell count is divided by the area traversed to provide a value proportional to the absolute white count of the specimen. FIG. 5b illustrates a search pattern which may be utilized. At the concentrations selected, 100 white blood cells will be encountered in approximately one inch of travel assuming a normal specimen. The nearly vertical lines of search shown in FIG. 5b may be spaced by as little as 100 microns providing a large search area without repetition. Concurrent operation of the stage and camera at the proper relative rates create a scan pattern such that strokes are approximately 2 microns apart guaranteeing no white cells are missed over the slide area traversed.

Referring to FIG. 4b, the camera 16 may be of the image dissector type. The object (cell) being scanned is imaged upon the photocathode 16b by lens 13. An electron lens (not shown) accelerates and focuses all electrons emitted from every point on the photocathode 16b to a corresponding point in the plane 16c of the dissecting aperture 16d. The electron image forming in plane 16c, current density modulated in accordance with the optical input radiation pattern 16e, is deflected across aperture 16d by x and y deflection coils 16f (only one coil being shown for purposes of simplicity.) The aperture thereby samples a small well-defined area of the image at any given instant. The electrons passing through aperture 16d are multiplied by a photomultiplier 16g (usually by factor of $10^5$ to $10^7$) whereby they emerge as a current in the anode circuit 16h whose current magnitude is determined by the optical modulation caused by the image. In a typical white cell search the stage 2 carrying the slide 30 moves at approximately 0.5 inches/second with a single motor step increment of 20 microns. This is approximately ten steps per white cell detection at the blood dilutions selected.

The video signals from camera 16 are amplified by amplifier 19 and fed into threshold amplifier 21. When threshold amplifier 21 senses a video signal greater than a pre-specified value the presence of desired cellular material is indicated and the stage 2 motion and camera search scan (FIG. 5) are stopped by the computer 6 and its interface 7. The transverse point at which the camera scan is stopped is recorded by computer 7.

The biological sample preparation process is designed to spread cells in a uniformly distributed manner so that they will rarely touch. Red cell analysis is performed through absorption in the reflective area of the microslide. The large density of red blood cells is such that a specific search for red cells is not required as it is for white blood cells and platelets. There will always be a number of red blood cells in the illuminated field. Thus, the computer system 6, 7 locates a red cell by setting the filters 9, 9a, 14 and 15 to detect hemoglobin absorption and then electronically positions the camera system 16, 17, 18 within the illuminated area when the reflective slide area is under examination. The high density of red cells also expedites the counting of red cells as follows:

1. Camera readings are enabled with the search spot stationary.
2. The stage is moved for a precisely controlled distance in x or y (2, 3, 4, 6, 7).
3. Each time a hemoglobin signal is detected via the camera system (16, 19, 21) a counter is incremented in the computer.
4. Use of the above count, the known area traced by the camera and the known volume of material (blood, stains, diluant, etc.) will permit the computation of the red blood count.

The mechanization of red cell counting is shown in FIGS. 4C, 10 (camera control), 11 (stage control), 12 (threshold detection). A mid-range value is set into both axes of the camera control logic FIG. 10 by the computer via the computer accumulator 62 and control logic 56. This causes the camera reading position to be centered over the light spot at position 64 of a possible 128 positions. Further, the mode flip-flop 64 will disable the clock gate 66 and inhibit changes of reading position.

Figure 12:
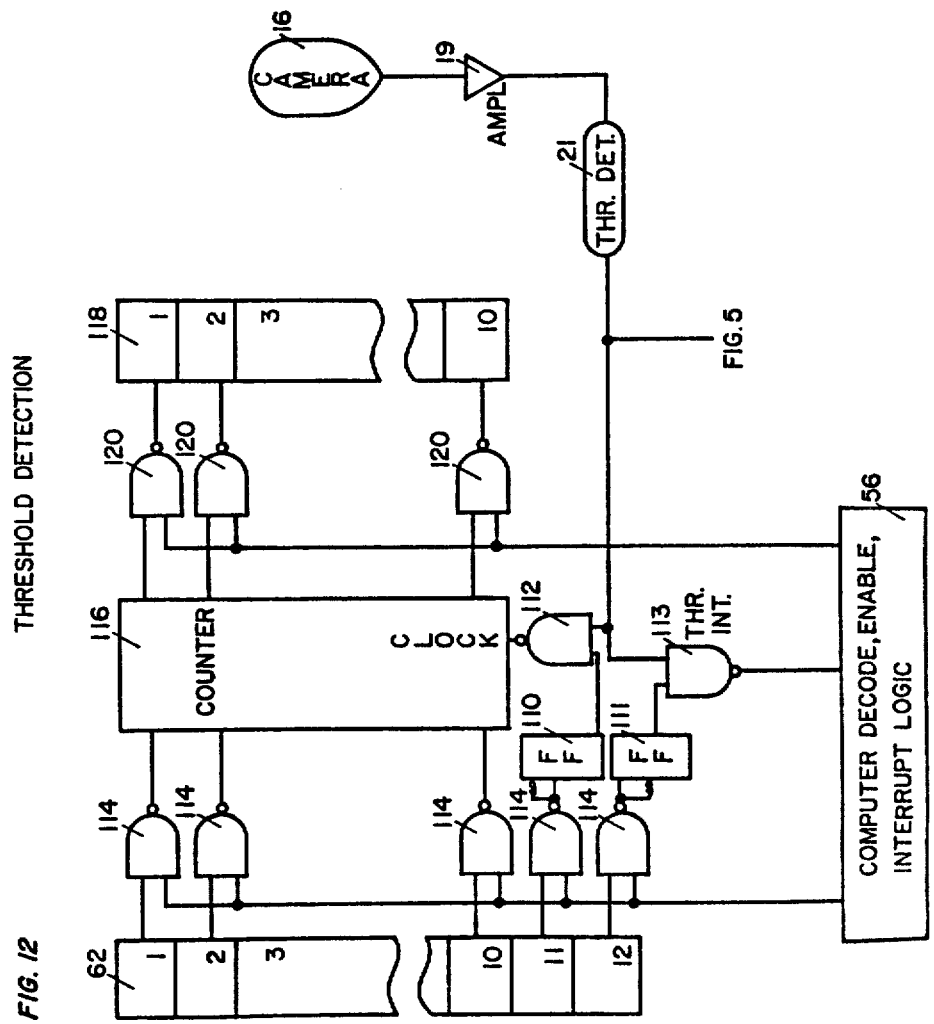
FIG. 12 is a schematic block diagram of a threshold detection circuit for use in the system of FIG. 4.

The threshold detection logic shown in FIG. 12 is then enabled. Zeros will be set into stages 1 through 10 of the accumulator 62. Stage 12 of the accumulator 11 will be set to enable counting of threshold crossings via flip-flop 110 and clock gate 112. Stage 12 will be set to inhibit individual threshold interrupts from entering the computer. Stage motion is then initiated to start a scan in the reflective half surface of the slide. A count of stage steps desired is set into accumulator, direction bit stage 11 is set and stepping is enabled via bit 12. In the concentrations of blood/SDS selected approximately 1,000 red cells will be detected per inch of travel if the specimen is normal. When a pattern strip is completed another may be initiated if insufficient cells had been detected.

In one implementation, red blood cell counting consists of the above steps (set camera, enable threshold detection, begin stage motion) plus the actual counting itself. This counting is performed via the threshold detection logic of FIG. 12. Illuminating filters are positioned such that light with a wavelength of approximately 408 nanometers wavelength illuminates the reflective area of the slide. This is reflected up to the face of the camera tube 16 and filtered so that only light at 408 nanometers is imaged. Dark spots caused by light absorbed by red cell hemoglobin and thus degraded form part of this image. As the stage moves the bright and dark areas pass over the face of the camera tube and are converted to a stream of electrons. A dimensionally limited number of electrons pass through a camera aperture and are amplified. The dimensional limit is small relative to the area cell. Thus a larger electrical signal emerges from the camera 16 when it is viewing the reflective area than when it is viewing a cell.

When this signal passes through amplifier 19 it enters threshold circuit 21. The threshold circuit may be a Schmitt trigger which operates to provide one logic level when an analog input is below a preset value and an inverse signal when it is above that value. Each time a high-low transition (reflective clear area to red cell absorption area) occurs a pulse enters the counter 116 through gate 112 and causes it to step. Each step represents the incremental count of one red cell.

After final termination of stage motion in which a known area is traversed, the contents of the counter 116 are read into the computer accumulator 110 via interface gates 120. The count is divided by the area traversed to provide a number proportional to the red blood cell count.

When a cell is located it may be necessary to scan and analyze it in detail. The illuminated area of the examining surface is large relative to the size of a cell (approximately 100:1) and the cell may be any place in this area. Therefore to improve efficiency it is desirable to accurately locate the cell prior to scanning it. A preferred method of locating the bounds of a cell is shown in FIG. 6. The interface electronics 6 are designed so that when a detection threshold occurs in amplifier 21 the camera position at the time of detection is stored (FIG. 6a Transverse Detection Point). Any positional uncertainty due to the stopping variation of the stage is resolved by electronic retracing of the stage motion at the location of the stored camera transverse detection position (TDP-FIG. 6a). When a point on the cell is found, the computer causes the camera to electronically scan and halt at a number of positions to determine the bounds of cellular material. A preferred method is to take readings at different angles (FIG. 6), moving along each of n vectors v (a preferred arrangement is with n equal to 8) until an end of material along that vector is ascertained.

Figure 13:
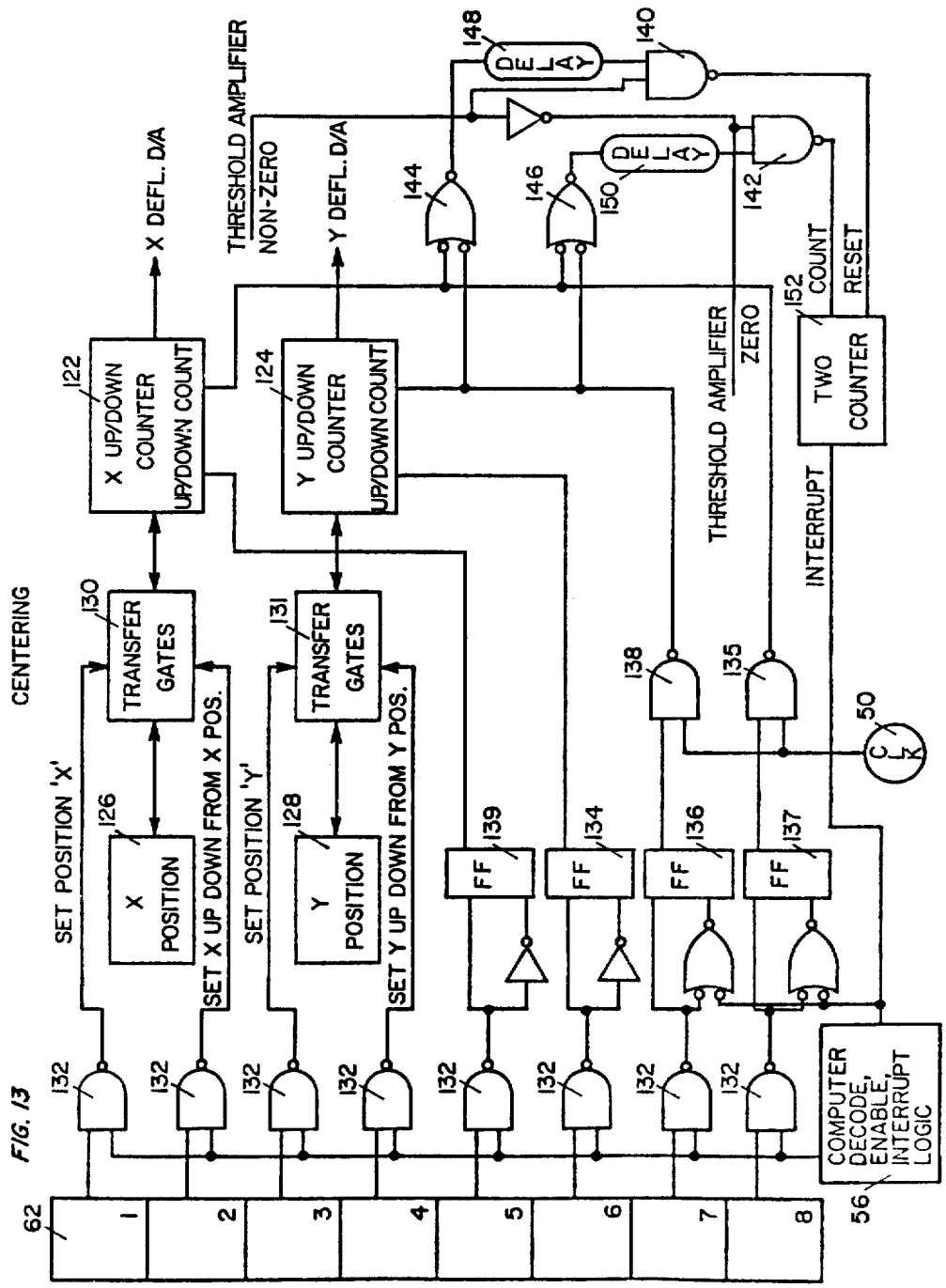
FIG. 13 is a schematic block diagram of a centering circuit for use in the system of FIG. 4.

FIG. 13 illustrates a method of implementing the centering (framing) function. The x-y camera position when detecting the cell of interest is stored in the x up/down counter 122 and in the y up/down counter 124 at the beginning of the centering procedure. The contents of the up/down counters are then transferred to the 'x' position register 126 and the 'y' position register 128. This occurs under control of the computer program via the computer control logic 56 when bits 1 and 3 of the computer accumulator 62 are set by the program. The above actions enable the position coordinates to be transmitted via the transfer gages 130 when these are enabled by the I/0 drivers 132.

Next, the centering pattern of FIG. 6 is created through use of the 'x' and 'y' deflection digital-to-analog converters D/AS. Referring to FIG. 6 the VI pattern is created first. This is accomplished by setting flip-flops 134 and 136. This sets the 'y' up-down counter 124 'up' and applies count pulses to it via gate 138. As the counter 124 steps, clock pulses are applied to sample threshold detector outputs via gates 140 and 142 nor gates 144 and 146 and delays 148 and 150. If the threshold amplifier indicates that material (DNA, RNA, Hemoglobin) is being read the two counter 152 is reset at the delayed clock time. If the threshold amplifier indicates no material, the two counter 152 is stepped twice by sequential "no material" readings it provides a terminating signal which resets flip-flop 136 (thus terminating stepping) and provides an interrupt to the computer via interrupt logic 56. The computer then causes the contents of the 'x' and 'y' up-down counters 12 and 124 to be sequentially read via control logic 56 and interface gates 88 FIG. 10 into the computer accumulator 156. These readings are at the periphery of the cell material examined plus two steps.

Next, the contents of the x position register 126 and the y position, register 128 are transferred to x up/down counter and y up/down counter 122 and 124 respectively. It does this by setting accumulator bits 2 and 4 and 62, transmitting these controls to the transfer gates 130 and 131 via the I/O drivers 138 and the control logic 56. When this is done the camera reading position is set to the initial condition for beginning a stroke; at the coordinate center of FIG. 6. V2 trace (FIG. 6) is initiated by setting flip-flop 134, flip-flop 136 and flip-flop 137 (FIG. 13). This causes the y up/down counter 124 to upcount and the x up/down counter 122 to down count. The process continues as previously described, until two sequential misses are detected in the two counter, 152 again defining the periphery of the cell. The computer is notified via the interrupt logic 56 and the data is read from the up/down counters 122 and 124.

The above process continues for traces v3, V4, V5, V6, V7 and V8 of FIG. 6. Traces are created by appropriately setting flip-flops 134, 136, 137, and 139 (FIG. 13) as follows:

| Trace | Flip-flops |
|-------|------------|
| V1 | 134, 136 |
| V2 | 134, 136, 137 |
| V3 | 137 |
| V4 | 136, 137 |
| V5 | 136 |
| V6 | 136, 137, 139 |
| V7 | 137, 139 |
| V8 | 134, 136, 137, 139 |

The computer uses a table of the above settings which are applied in series. The computer causes the following sequence to occur:

1. It causes the transfer of the x and y up/down counters 122 and 124 to x and y position registers 126 and 128 via transfer gates 130 and 131 through use of the accumulator 62, I/O drivers 132 and computer control logic 56.

2. It sets the direction of and initiates traces V1 through V8 (FIG. 6) through application of table entries for flip-flop settings 134, 136, 137, 139.

3. It reads the contents of the x and y up/down counters via control logic 56 and I/O drivers 88 into computer accumulator 156 after the occurance of an end-of-material interrupt via the two counter 152 and the computer control logic 56.

4. It stores the end-of-material positions in a buffer table.

5. When all traces have been read it scans the table for minimum and maximum x and y positions. This minima and maxima are stored as frame limits for later use by the dissection programs.

When maximum bounds (plus a small allowance) are found the frame is defined as the minimum and maximum of x and the minimum and maximum of y. Framing must be done twice for a white cell, i.e. once for the nucleus and once for the cytoplasm.

After a cell is framed the microscope is focused using the point of maximum reading amplitude of the analog to digital converter 22 found during framing. Focusing is done by motor 5 under control of computer (7) through interface (6). This is accomplished through control of the motion of the stage in the z direction while concurrently reading the output of the A/D. When a "z" position is found at which the A/D reading of the fluorescent response of the cell is maximized the microscope is in focus. FIG. 8 shows how focusing is determined when sensing DNA amplitude which is plotted against the Z position of the slide, the z movement being controlled by motor 5.

Figure 14:
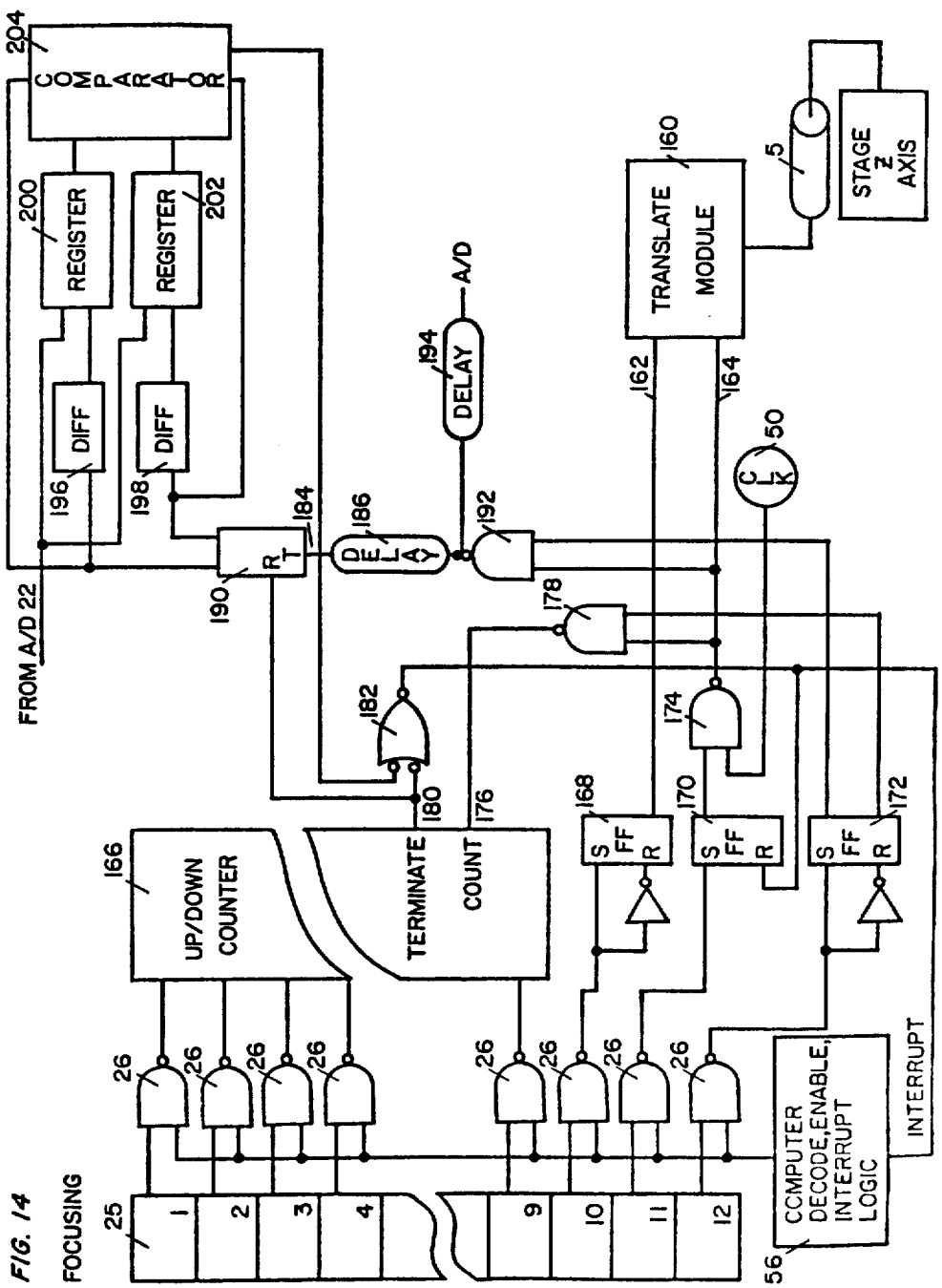
FIG. 14 is a schematic block diagram of a focusing circuit for use in the system of FIG. 4.

FIG. 14 illustrates a method of implementing focusing by controlling the 'z' stage motor 5. The stage 'z' axis is controlled by stepper motor 5 under control of a translator module. The motor 5 is capable of moving the 'z' axis up-ward or downward at a rate of several hundred 1.8 degree steps per second. A gearing system not shown within the stage converts this angular movement to vertical steps of several tenth of a micron each. Inputs to the translator module are a direction-of-rotation level 164 and step pulses 166.

Initially the step motor 5 is moved in a direction such that the 'z' axis is moved downward to a point where the cell is well out of focus. This is accomplished by setting counter 166 to a fixed number from the computer. Subsequently flip-flop 168 and flip-flop 170 are activated and flip-flop 172 is deactivated such that the direction-of-rotation level 162 is properly set and step pulses 164 are activated from the clock via gate 174. At the same time the step pulses 176 are applied to counter 166 via gate 174 and gate 178. When the counter reaches its terminal count 180 flip-flop 180 is reset through 'nor' circuit 182 and the step pulses deactivated. The computer is notified of completion of descending sequence through I/O and control logic 56.

The step motor is then moved in a direction such that the 'z' axis of the stage is moved upward to bring the cell into focus. Flip-flip 168 is activated such that the direction of rotation level 162 is proper. In addition flip-flop 170 is activated to allow step pulses to translator module 160. Flip-flop 172 is activated to enable step pulses 184 through delay 186 via gate 192 triggerable flip-flop 190. Triggerable flip-flop 190 had been previously reset by the terminal count of counter 166. Delay 186 allows the stage to move to its next position prior to sampling the contents of A/D 22 (FIG. 4). A pulse passed through another delay 194 triggers A/D conversion. The differentiators 196 and 198 take the rising edges of flip-flop 190 and transfer the content of A/D 22 (FIG. 4) alternately into registers 200 and 202. Comparator 204 senses whether the new A/D out-put is less than the previous output. When this occurs step pulses 164 are terminated through the resetting of flip-flop 170 via gate 182. The computer is notified through interupt logic 56 that focusing is complete. This places the cell one upward step beyond the peak of the focus curve of FIG. 8. Since this peak is many microns wide, compared to the vertical upward movement (several tenths of microns) focusing is sufficient to continue operation of the CDM.

For each white cell, the microscope is focused. The computer 7 through interface (6) controls the camera (16) through the D/A's (18) and x-y deflection amplifiers (17) to perform a dense but non-overlapping raster scan of all of the material within the frame. Video signals representing the amplitude of fluorescence within the camera reading aperture are amplified by amplifier (19) and converted to digital representations by A/D converter (22) and accepted by the computer (7) through interface (6). Due to the system characteristics (stain, speciman preparation, filtering, etc.) readings can be made on the various materials at high signal-to-noise ratios with minimal mutual interference. White cells will be scanned for hemoglobin and RNA related materials. Platelets will be scanned for RNA related materials.

Preconditions for WBC nuclear dissection are (a) a motionless stage, (b) DNA illuminating and reading filters in position, (c) focus, and (d) framing of a WBC nucleus. FIG. 15 illustrates a nucleus which has been framed and focused. In the process of dissection the computer controls the camera (16) via the deflection circuitry to permit a selected small area in the order of 0.7×0.7 microns within the frame perimeter to be examined to measure the amount of light emitted from the area. The photo image within the area is converted to an amplified electron stream by the camera (16). This analog voltage is amplified in amplifier (19) and is entered into an analog to digital converter 22. State-of-the-art A/D converters may be purchased in versions which will convert to digital in various binary bit ranges. Versions useful in this application are in the six to ten bit area.

FIG. 16 illustrates the interface of an eight bit converter with a computer. The computer provides a pulse to the convert input of the A/D converter. The A/D will begin converting the immediate analog input to a digital representation. When the A/D conversion is completed a signal is provided to the computer. The computer will then cause the digital value stored in the A/D converter to be entered into the computer accumulator 62 via interface logic and gates.

As shown in FIG. 15, the CDM system will sequentially read a digital representation of the amplitude of each point in the frame into the computer memory (not shown). The sequence of readings can, for example, be initiated at column C1, row R1 and R1 through Rm will be entered into the computer memory. This will be followed by C2R1 through Rm, etc. until CnRm is reached. At this point reading is completed with each activated memory cell in the table containing an amplitude and, in effect, the table representing a three dimensional (CxRx amplitude) memory map of the contents of the frame.

Positioning to a reading point is via the camera control logic illustrated in FIG. 10. Using the frame boundaries resulting from the framing procedure as limits the program positions for reading C1R1 by placing seven data bits into the accumulator 62 and setting mode bit 8 to inhibit clock stepping pulses. A subsequent command via control logic 56 and interface gates jams the seven accumulator bits into the counter 68. The counter 68 (here used as a storage register) output sets the D/A (70) to provide an analog output which causes appropriate deflection signals to be applied to the camera. The positioning procedure is applied to both axes for each point in the frame. Using state-of-the-art techniques, positioning errors of less than one percent are easily attainable.

As the amplitude values are entered into the computer they are examined, computations are performed and decisions are made on a point by point and on a total cell basis. Each reading point storage word contains amplitude information and indicators. In a PDP-8M computer approximately 50 microseconds are required per reading point in the following WBC dissection tasks:

1. The digitized amplitude value is entered from the A/D and a constant representing a minimum acceptable reading (representing a signal above the system's noise level) is subtracted.

2. If the reading is inadequate the tests are made to determine if the previous point in this column was adequate (i.e., inside the material of interest) and if the adjacent point in the previous column was adequate. If the previous point in the column was adequate an indicator is set in its word and an edge count is incremented. If the adjacent point in the previous column is adequate and its edge indicator was not previously set then it is set and the edge count is incremented.

3. If the reading is adequate tests are made to determine if the previous point in this column was adequate (i.e. inside the material of interest) and if the adjacent point in the previous column was adequate. If either were inadequate the edge indicator in the present point is set and the edge count is incremented.

4. If the reading is adequate it is processed as follows:
(a) a register in the computer in which a sum of readings is maintained is incremented by the present reading. When readings are complete this register (not shown) will contain a summation of amplitude representing composite DNA (if the nucleus is being scanned) or RNA (if the cytoplasm is being scanned).

(b) A register in which a count of adequate readings is maintained is incremented. The increment is by one half if the reading is an edge point. When readings are complete this register will contain a summation representative of nuclear area (if the system is in DNA scan) or total cell area if the system is in the cytoplasm scan mode.

(c) Two histogram tables, one of nuclear readings, the other of cytoplasmic readings, are generated. Edge points are not included in the histograms. The histogram tables are prepared by taking the memory address of the first location of the appropriate (nucleus or cytoplasm) histogram table, adding the amplitude value to this address and, incrementing the memory location whose address is thus computed. The eight bits of amplitude read permit 256 location histograms to be prepared. For any practical purposes a shorter table is satisfactory, the table size may be reduced by rounding or shifting the amplitude word prior to generating the histogram address.

(d) A lobe count is developed during nuclear dissection. The procedure is as follows. When the first adequate nuclear point is read it is assigned a lobe identification number of '1' (provision is made for a maximum of seven lobes). During the scan each adequate touching point, following in the column is also assigned the number '1'. When a non-contacting adequate point is found it is assigned provisional lobe identification '2' and treated similarly. Subsequent provisional lobes are assigned new identifications as they occur. Occasionally one lobe is temporarily multiply identified. For example, during the scan of column Cr (FIG. 7I) a new lobe identification '2' is given in row Rs. The system will consider two lobes to be present until a subsequent column at which time it is found that lobe '1' and provisional lobe '2' are in contact and are therefore in reality one lobe. Lobe '2' entries are then reidentified to be of lobe '1'. At the end of nuclear search a count of lobe numbers finally assigned provides the cell lobe count.

After the above information is collected for the nucleus, per previous descriptions, filters are switched, the cell is refocused and reframed and the cell cytoplasm is dissected. The above procedure (steps 1-3) is repeated with the exception that the lobe counting procedure is not followed for the cytoplasm. Cell identification is then performed.

The method of identifying a dissected cell is to compare the parameters collected with prestored limits based on the previously measured characteristics of white blood cells. The identification procedure is, in general, as follows:

1. The cell RNA summation is divided by the DNA summation. The resulting value is compared with upper and lower limits for each type of cell. If the cell values are outside of all stored limits it is designated unknown and all parameters are prepared for printing. Additionally the stage position at which the cell was found is printed to permit subsequent examination by the clinician. If as occurs in a small number of cases, the RNA/DNA reading is in an overlap of limits, the cell will be identified through additional tests. Over 90% correct identification of normal cells is attained through use of the RNA/DNA ratio.

Thus in FIG. 9, the various RNA amplitude values are summed in the arithmetic unit 57. Similarly the various DNA amplitudes are also summed in the arithmetic unit 57. These two summations are then divided for each cell and the ratio is compared with a table 59 in the computer memory 55. The relation of RNA to DNA is plotted in FIG. 17 to show the separations that occur in the different white cells in a differential count. The cells 220 are lymphocytes, the cells 222 are monocytes, the cells 224 are neutrophils whereas the cells 226 and 228 are eosinophils and basophils respectively. It is to be noted that significant separations occur in the spacings of these white cells on the graph. The graph is actually the inverse of the RNA to DNA ratio to illustrate the separations more clearly.

2. Cell nuclear and cytoplasm textural parameters are then examined and compared with limits. Histograms provide indications of smoothness and degree of coarseness. For example, the cytoplasm of a lymphocyte contains few granules and most points of its histogram concentrate in a low amplitude area. The cytoplasm of a nutrophil is granular so that readings will spread more widely over the histogram. The nuclear material of a lymphoctye is texturally smoother than that of a monocyte, etc.

3. The summed amplitude of the nucleus is divided by the count of adequate nuclear points. The summed amplitude of the cytoplasm is divided by the count of adequate cytoplasm points. Both results, in actuality providing average densities of DNA and RNA responses, are compared with limits characteristic of the several cell types and their level of maturation.

4. A ratio of the count of adequate points to the count of edge points is made for the nucleus and compared with sets of limits selected on the basis of nuclear area within cell types. These values indicate the departure of the nucleus from "roundness" and are used primarily in determining maturation. For example, the immature granulocyte (myclocyte) is round. In maturation it becomes indented (metomyclocyte) and then becomes a band cell in the course of development to a mature lobed cell. Each stage (for the neutrophil, basophil and eosinophil) has characteristic out-of-round ratios.

5. The lobe count of a granulocyte is indicative of its maturity. A fully mature neutrophil has three or four lobes. If the lobe count is beyond five the cell is abnormal.

When testing against limits is completed, a register representing a cell type and maturation is incremented. If the cell is unknown or suspicious, a count is incremented and measured cell parameters and cell location is prepared for printout to permit subsequent manual examination.

The dissection, analysis and counting of RBC is performed in the reflective area of the slide. Illuminating and barrier filters are set to the peak absorption wavelength of hemoglobin at 408 nanometers. WBC and platelets are, in practice, invisible at this wavelength and thus do not interfere with RBC analysis. The search for RBCs is straightforward since, at the blood dilutions utilized, dozens of RBC will normally be located in the illuminated area. To simplify processing and to limit RNA burnoff from reticulocytes only a small number of RBC will be examined in an illuminated area prior to moving several stage steps to an adjacent area.

In selecting an RBC for analysis the computer will move the image over the camera reading aperture and monitor amplitudes via A/D converter 205 (FIG. 6). Points of the reflective surface not covered by RBCs are relatively much brighter than those upon which an RBC rests. When a dimmed point is detected denoting the presence of an RBC, centering will begin. The procedure for the centering of a RBC is logically similar to the procedure used for WBC except that examination is for dim rather than bright areas. A further difference is that if the frame area is larger than 120 microns the assumption is made that two cells are close and may be touching. This occurs in a small percentage of centering attempts. In this event the RBC under examination is dropped and another is found.

Focusing is performed on a bright reflective spot adjacent to the cell in a manner identical to that used in WBC focusing with one exception. After focusing, as previously described, occurs the stage is moved down approximately 0.4 microns so that focus will be in the center of the plane of the cell rather than on the slide surface.

After focusing is completed, the RBC is dissected in a point by point manner as described for the WBC. A table of 'C'×'R' amplitudes of absorbance is constructed as follows:

1. The amplitude responses of several points surrounding the cell and not masked by hemoglobin are collected and averaged to provide a mean reflectivity value.

2. As points within the frame are read they are subtracted from the reflectivity value. The resulting value is tested against a constant representing a minimum acceptable absorbance to determine if the point read is within the cell area.

3. If the absorption is inadequate tests are made to determine if the previous point in this column is adequate (i.e. inside the cell area) and if the adjacent point in the previous column is adequate. If the previous point was adequate an edge indicator is set in its word and an edge count is incremented. If the adjacent point in the previous column is adequate and its edge indicator was not previously set the program sets it and increments the edge count.

4. If the absorption is adequate tests are made to determine if the previous point in this column was adequate (i.e. inside the cell) and if the adjacent point in the previous column was adequate. If either were inadequate the edge indicator in the present point is set and the edge count is incremented.

5. If the absorption of a point is adequate it is processed in the following manner:

(a) As the illuminating light passes through the cell some is absorbed by the hemoglobin through which it passes. It is reflected from the mirrored surface and passes through the cell again and a second absorption occurs. In this procedure the cell acts as a neutral density filter where: Density = $\frac{1}{2}$ log (I1/I2) wherein:

$I_1$ = mean reflectivity value from the mirrored surface, and $I_2$ = reflectivity value after light has passed through the cell a second time. Each density value is calculated and stored for each point in the cell.

(b) A register in which a sum of converted reading amplitudes is maintained is incremented by the input. When all readings have been taken on the cell, the final summation in this register is proportional to hemoglobin content of the cell.

(c) Hemoglobin absorbs light uniformly as a function of the length of the column of hemoglobin traversed by the light. This column length determination is a function of the calculated density value used as a look-up index to a table of predetermined length values. Using this information, each reading is converted from an amount of hemoglobin to a volume measurement; the volume being the reading spot area multiplied by the thickness (column length) of the cell at the reading point. The converted value is added to a register whose final sum after the cell is completely examined is proportional to the volume of the cell.

(d) A register in which a count of 'adequate' readings is made is incremented. The increment is by one one half unit if the reading is an edge point. When readings are complete the register will contain a number representing the area of the cell.

(e) A histogram of non-edge point reading values is created.

6. Following the hemoglobin scan an RNA dissection is performed. The illuminating filter is set to 465 nanometers and the barrier filter to 630 nanometers. The cell is then scanned within the frame previously generated for the hemoglobin dissection and at the same focus setting. In the scan a constant representing a minimum acceptable value is subtracted from the reading. If the reading proves adequate it is added to a register whose final total represents the RNA content of the cell.

After the above date has been collected, the computer divides the count of adequate readings by the edge point count. The ratio is compared with prestored limits. If the limits are exceeded the cell is substantially out of round. Further, the histogram is examined. The histogram of RBC hemoglobin for normal cells is quite regular and repeatable as the cell is a biconcave disc. Deviations demonstrate that the cell is a spherocyte, target cell, nucleated, etc. The ability to perform the morphological procedures described is, in great part, made possible by the specimen preparation technique which prepares the cells in a flat, uniformly dispersed, easily analyzed manner. The presence of a significant numbers of irregularly shaped cells is indicative of an abnormal condition. Such findings are printed as part of the test result memory.

A substantial number (approximately 100) of RBCs are dissected and analyzed in the manner described. After this is done cell volumes are averaged to provide a value proportional to mean corpuscular hemoglobin (MCH). A value proportional to hematocrit is generated by multiplying the MCV by the RBC count and utilizing the result as a lookup key in a table of prestored hematocrit values. Counts of reticulocytes binned through use of composite RNA readings are also provided.

The computer (7), in one preferred embodiment, may be a small digital computer with a core memory capacity of 8,192 twelve or sixteen bit words, such as a PDP8 computer. It is preferably equipped with an input/output typewriter and, as required, other peripheral equipment such as magnetic tapes (for data storage) and video displays (for simultaneous or subsequent observation of collected data).

FIG. 4c shows the interface 6 in greater detail which comprises counter/registers CR and/or motor driving circuits MD for the motors 3, 4, 5 9a and 15. Clocking circuits CC control the stepping, loading, and unloading of the counter/registers CR.

The computer acts, as previously described, to control the system in the collection of information. After the scanned data for a cell is collected in memory it is analyzed, and identified through determination of the nature of the fluorescent responses of the cell, its size (nucleus and cytoplasm), lobe count, texture, shape and other characteristics. Counts of the cell types detected, differentiating normals, abnormals and levels of cell maturation, are compiled and printed on the input-output typewriter. Additional computed information such as mean corpuscular volume, hematocrit, etc. are also generated and provided. Table 2 lists the counts and measurements provided for.

Tables 3, 4, and 5 show the method and program steps in white blood cell, red blood cell, differential count and platelet analysis.

TABLE 2

TESTS TO BE PERFORMED BY CDM

White blood cell count
Differential count (Abnormal morphologies will be noted if not identified
Eosinophils } itemizing } Myelocytes
Neutrophils                Staff Cells
Basophils                  Lobe Counts
Monocytes
Large Lymphocytes
Small Lymphocytes
Plasma Cell Count
Platelet Count
Platelet Evaluation
Hematocrit
Hemoglobin
RBC Morphology
RBC Count
Reticulocyte Count
Mean Corpuscular Volume
Mean Corpuscular Hemoglobin
Mean Corpuscular Hemoglobin Concentration

TABLE 3

WHITE BLOOD COUNT

1. Set filters at DNA (subroutine)
2. Set up search pattern
3. Search for nucleus
4. Detection interrupt-find true detection position

TABLE 3-continued
WHITE BLOOD COUNT

| | (subroutine) |
|---|---|
| 5. | Frame nucleus (subroutine) |
| 6. | Focus on high amplitude point (subroutine) |
| 7. | Dissect nucleus (DNA) (subroutine) |
| 8. | Switch filters to RNA (subroutine) |
| 9. | Expand frame or reframe |
| 10. | Dissect cytoplasm (RNA) (subroutine) |
| 11. | Switch filters to DNA (subroutine) |
| 12. | Move stage 2 steps to avoid having next cell polluted by present analysis due to burn off |
| 13. | Analyze cell and type it using RNA/DNA ratio |
| 14. | Compute white count according to area searched |

TABLE 4
RED BLOOD COUNT

| 1. | Set filters for hemoglobin (subroutine) |
|---|---|
| 2. | Set up search pattern to run for specific distance |
| 3. | Count detections |
| 4. | Move stage to fresh area and stop |
| 5. | Set up red cell search-move light only |
| 6. | Frame cell (subroutine) |
| 7. | Focus (subroutine) |
| 8. | Dissect hemogloblin (subroutine) |
| 9. | Switch filters to RNA (subroutine) |
| 10. | Dissect RNA (subroutine) |
| 11. | Switch filters to hemoglobin (subroutine) |
| 12. | Analyze and type cell |
| 13. | Compute mean corpuscular volume and hemotocrit |

TABLE 5
PLATELET ANALYSIS

| 1. | Set filters for RNA (subroutine) |
|---|---|
| 2. | Set up search pattern for platelet analysis |
| 3. | Count detections-keeping track of area |
| 4. | Detection interrupt-back up light (not stage) to find true detection position (subroutine) |
| 5. | Frame cell (subroutine) |
| 6. | Focus (subroutine) |
| 7. | Dissect (subroutine) |
| 8. | Analyze |

Obviously, by changing the criteria by which cells are distinguished from each other, the power of the system as an aid to diagnosis can be enhanced. Any type of cell or cell borne parasite, human or animal, can be analyzed by reprogramming and, in some cases, by modifying the sample preparation procedure.

Although there has been described a preferred embodiment of this novel invention, many variations and modifications will now be apparent to those skilled in the art. Therefore, this invention is to be limited, not by the specific disclosure herein, but only by the appended claims.

What is claimed is:

1. Apparatus for facilitating the analysis of a sample of cellular material, said sample comprising a precipitation of cells stained with material so as to fluoresce when illuminated by light of predetermined wavelengths wherein the wavelength of the light emitted by the stains is determined by the type of cellular material to which the stain adheres, comprising:

a microscope slide member (whose) having a unitary examining surface (includes) including at least a first area portion having a light reflective coating and at least a second area portion having a non-reflective surface said first and second area portions being substantially coplanar and adjacent each other so that, a sample of said cellular material is deposited upon adjacent reflective and non-reflective portions of said examining surface, whereby the reflective area of the slide facilitates examination of individual cells through an absorption technique, and the nonreflective area of the slide facilitates examination of individual cells through the examination of the fluorescent response of cellular materials.

2. The slide of claim 1 wherein the stain material includes at least one fluorescent acridine dye.

3. The slide of claim 1 wherein said stain material is taken from the group comprising corophosphine and acridine orange.

4. The slide of claim 3 wherein:

said stained specimen is spun upon the slide to distribute the cells uniformly in a manner proportional to the total number of said cells in said specimen whereby a first portion of the said specimen is deposited upon the reflective surface and a second portion of the specimen is deposited upon the slide adjacent to the reflective surface;

and wherein said slide is scanned with imaged light to sequentially measure absorbed and fluorescing light from the sample.

5. The apparatus in accordance with claim 1 wherein said microscope slide includes a third area portion having a frosted surface to permit writing thereon.

6. The apparatus in accordance with claim 1 wherein said second area portion is transparent.

7. The apparatus in accordance with claim 1 wherein said first area portion is coated with evaporated aluminum.

8. The apparatus in accordance with claim 1 wherein said first area portion is coated with a reflective mylar tape.

9. The apparatus in accordance with claim 1 wherein said microscope slide member is acrylic plastic.

10. The apparatus in accordance with claim 1 wherein said microscope slide member is substantially rectuangular is shape having one corner cut off to permit insertion into a microscope in a prescribed manner.

* * * * *